(12) United States Patent
McLean et al.

(10) Patent No.: US 7,388,197 B2
(45) Date of Patent: Jun. 17, 2008

(54) MULTIPLEX DATA ACQUISITION MODES FOR ION MOBILITY-MASS SPECTROMETRY

(75) Inventors: John A. McLean, Bryan, TX (US); David H. Russell, College Station, TX (US); Thomas F. Egan, Houston, TX (US); Michael V. Ugarov, Houston, TX (US); J. A. Schultz, Houston, TX (US)

(73) Assignee: Ionwerks, Inc., Houston, TX (US)

( * ) Notice: Subject to any disclaimer, the term of this patent is extended or adjusted under 35 U.S.C. 154(b) by 292 days.

(21) Appl. No.: 11/191,666

(22) Filed: Jul. 27, 2005

(65) Prior Publication Data

US 2006/0024720 A1    Feb. 2, 2006

Related U.S. Application Data

(60) Provisional application No. 60/591,568, filed on Jul. 27, 2004.

(51) Int. Cl.
*B01D 59/44* (2006.01)
*H01J 49/00* (2006.01)

(52) U.S. Cl. .............. 250/293; 250/281; 250/288; 250/290; 250/292; 250/294

(58) Field of Classification Search ............ 250/292, 250/293, 294
See application file for complete search history.

(56) References Cited

U.S. PATENT DOCUMENTS 6,683,299 B2 *   1/2004   Fuhrer et al. ............ 250/287
2005/0029445 A1   2/2005   Lee et al.

* cited by examiner

*Primary Examiner*—David A. Vanore
(74) *Attorney, Agent, or Firm*—Fulbright & Jaworski, LLP

(57) ABSTRACT

A method and apparatus for multiplexed data acquisition for gas-phase ion mobility coupled with mass spectrometry is described. Ion packets are injected into an ion mobility drift chamber at a rate faster than the ion mobility separation arrival time distribution. The convoluted arrival time distributions thus generated are deconvoluted by a mass spectrometer and post-processing algorithms.

6 Claims, 19 Drawing Sheets

MULTIPLEX DATA ACQUISITION MODES FOR ION MOBILITY-MASS SPECTROMETRY

CROSS-REFERENCE TO RELATED APPLICATIONS

This application claims priority to U.S. provisional application Ser. No. 60/591,568, filed Jul. 27, 2004.

TECHNICAL FIELD

This invention describes a method for multiplexed data acquisition for gas-phase ion mobility coupled with mass spectrometry. Ion packets are injected into an ion mobility drift chamber at a rate faster than the ion mobility separation arrival time distribution. The convoluted arrival time distributions thus generated are deconvoluted by a mass spectrometer and post-processing algorithms. Sensitivity and throughput can be improved by factors of ca. 10 to 1000 by using the correlated data acquisition modes of this invention and further improvements can be gained by multiplexing ion mobility-mass spectrometry/mass spectrometry techniques for nearly simultaneous parent and daughter ion analysis.

BACKGROUND OF THE INVENTION

Two-dimensional gas-phase separations based on ion mobility (IM)-time-of-flight mass spectrometry (TOFMS) have demonstrated unique potential in the analysis of a wide range of materials and more recently in the analysis of complex mixtures of biomolecules [T. Wyttenbach and M. T. Bowers, Gas-Phase Conformations: The Ion Mobility/Ion Chromatography Method, Top. Curr. Chem. 225, 207-232 (2003) and references therein; and C. S. Hoaglund-Hyzer, A. E. Counterman, and D. E. Clemmer, Anhydrous Protein Ions, Chem. Rev. 99, 3037-3079 (1999) and references therein.]

Gas-phase ion mobility (IM) provides ion separation by generating or injecting ions (and gaseous neutral species) in/into a gas-filled drift tube (typically 1 to 760 Torr) where they migrate under the influence of a weak electrostatic-field (typically 1 to 100 V cm$^{-1}$ Torr-1) and are impeded by collisions with the background gas. Biologically relevant ions are injected into the drift cell by using pulsed ion sources (e.g., matrix assisted laser desorption/ionization (MALDI)) or by pulsing a continuous ion source (e.g., electrospray (ESI) or ion spray). Other techniques to generate biologically relevant ions (and gaseous neutral species) may be used, such as surface enhanced laser desorption/ionization (SELDI). Other nonlimiting examples include atmospheric pressure MALDI, ultraviolet MALDI, infrared MALDI, direct LDI (laser desorption/ionization), nanospray, photoionization, multiphoton ionization, resonance ionization, thermal ionization, surface ionization, electric field ionization, chemical ionization, atmospheric pressure chemical ionization, radioactive ionization, discharge arc/spark ionization, laser induced breakdown ionization, inductively coupled plasma ionization, direct current plasma ionization, capacitively coupled plasma ionization, glow discharge ionization, microwave plasma ionization, and any combinations thereof. The theory of IM is fully developed in texts by Mason and McDaniel [E. W. McDaniel and E. A. Mason, The Mobility and Diffusion of Ions in Gases, Wiley, New York, N.Y. (1973); E. A. Mason and E. W. McDaniel, Transport Properties of Ions in Gases, John Wiley & Sons, Inc., New York, N.Y. (1988)], and the combination of IM with quadrupole mass spectrometry and subsequently time-of-flight mass spectrometry (TOFMS) dates back to the early 1960's [W. S. Barnes, D. W. Martin, and E. W. McDaniel, Mass Spectrographic Identification of the Ion Observed in Hydrogen Mobility Experiments, Phys. Rev. Lett. 6, 110-111 (1961); K. B. McAfee Jr. and D. Edelson, Identification and Mobility of Ions in a Townsend Discharge by Time-Resolved Mass Spectrometry, Proc. Phys. Soc. London 81, 382-384 (1963)]. The mobility (K) of an ion is determined by the ratio of the drift velocity ($v_d$) to the electric field strength (E):

$$K = \frac{v_d}{E} \quad [1]$$

When the ion-neutral collision energy nears the thermal energy of the system, the mobility approaches the so-called "low-field" limit and can be related to the collision cross-section ($\Omega$), or apparent surface area, of the ion:

$$K = \frac{3}{16} \frac{q}{N} \left( \frac{1}{\mu} \frac{2\pi}{k_B T} \right)^{\frac{1}{2}} \frac{1}{\Omega} \quad [2]$$

Where N is the number density of the drift gas, q is the ion charge (in MS techniques this is typically termed ze), $\mu$ is the reduced mass of the ion-neutral collision pair, $k_b$ is Boltzmann's constant, and T is the temperature of the system. Thus, IM provides separation selectivity based on the charge-to-collision cross-section (q/$\Omega$) ratio of the analyte ion in a particular background drift gas, in contrast with MS based ion separation, which separates analyte ions on the basis of their mass-to-charge (m/z) ratio.

Analyte selectivity based on ion mobility separation provides several important advantages over prior art solution-based purification (e.g., high performance liquid chromatography) or gas-based mass-to-charge selection (i.e., MS) of biological molecules: (i) in many cases isobaric and isoform species (e.g., structural and/or conformational isomers) can be separated [F. W. Karasek and D. M. Kane, Plasma Chromatography of Isomeric Halogenated Nitrobenzenes, Anal. Chem. 46, 780-782 (1974); J. C. Tou and G. U. Boggs, Determination of Sub Parts-Per-Million Levels of Sec-butyl Chloropiphenyl Oxides in Biological Tissues by Plasma Chromatography, Anal. Chem. 48, 1351-1357 (1976); T. W. Carr, Plasma Chromatography of Isomeric Dihalogenated Benzene, J. Chrom. Sci. 15, 85-88 (1977); D. F. Hagen, Characterization of Isomeric Compounds by Gas and Plasma Chromatography, Anal. Chem. 51, 870-874 (1979)], (ii) the separation mechanism does not rely on solution-phase physical properties (e.g., hydropathy, isoelectric point, affinity, etc.) [E. W. McDaniel and E. A. Mason, The Mobility and Diffusion of Ions in Gases, Wiley, New York, N.Y. (1973); E. A. Mason and E. W. McDaniel, Transport Properties of Ions in Gases, John Wiley & Sons, Inc., New York, N.Y. (1988)], (iii) it is amenable to a wide variety of molecular classes or complex mixtures thereof (e.g., proteins, lipids, oligonucleotides, carbohydrates, etc.) [J. M. Koomen, B. T. Ruotolo, K. J. Gillig, J. A. McLean, D. H. Russell, M. Kang, K. R. Dunbar, K. Fuhrer, M. Gonin, and J. A. Schultz, Oligonucleotide Analysis with MALDI-Ion Mobility-TOFMS, Anal. Bioanal. Chem. 373, 612-617 (2002)], and (iv) in many cases it is sensitive and selective for post-translationally modified peptides (or proteins) [B. T.

Ruotolo, G. F. Verbeck, L. M. Thompson, A. S. Woods, K. J. Gillig, and D. H. Russell, *Distinguishing Between Phosphorylated and Nonphosphorylated Peptides with Ion Mobility-Mass Spectrometry*, J. Proteome Res. 1, 303-306 (2002)].

Contemporary IM and IM-MS is performed by injecting ions into the drift cell slower than the transient rate of ion separation necessary to retain analyte injection/detection time correlation (i.e., at a rate $<t_d^{-1}$, where $t_d$ is the drift time of the ions through the mobility cell). Traditionally this is termed the "pulse-and-wait" approach. However, significant enhancements in signal-to-noise (S/N) and throughput can be realized by adapting multiplex data acquisition methods to IM-MS. Fourier transform (FT), Hadamard transform (HT), and correlation techniques are commonly used in optical and molecular spectroscopy, but their application to mass spectrometry has, until recently, been limited to FT-ion cyclotron resonance-MS [M. Harwit and N. J. A. Sloane, *Hadamard Transform Optics*, Academic Press, New York, N.Y. (1979); A. G. Marshall, Ed., Fourier, *Hadamard, and Hilbert Transforms in Chemistry*, Plenum Press, New York, N.Y. (1982); A. G. Marshall and F. R. Verdun, *Fourier Transforms in NMR, Optical, and Mass Spectrometry*, Elsevier, New York, N.Y. (1990)]. The Fellgett advantage afforded by these techniques can also be realized by injecting ion packets into the IM drift cell or TOFMS drift tube faster than the sequential (i.e., pulse-and-wait) duty cycle. Although both techniques achieve separation based on time dispersion of the analytes, multiplexing of IMS or TOFMS have only been described as distinctly separate experiments.

For example, Hill and coworkers have demonstrated a 1.4-fold increase in IM sensitivity by in-phase frequency sweeping of ion gates (Bradbury-Nielsen design [N. E. Brabury and R. A. Nielsen, *Absolute Values of the Electron Mobility in Hydrogen*, Phys. Rev. 49, 388-393 (1936)]) at the entrance and exit of the drift cell. The ion mobility arrival time distributions were reconstructed from the frequency-domain interferogram by application of a Fourier transform [F. J. Knorr, R. L. Eatherton, W. F. Siems, and H. H. Hill Jr., *Fourier Transform Ion Mobility Spectrometry*, Anal. Chem. 57, 402-406 (1985); R. L. Eatherton, W. F. Siems, and H. H. Hill Jr., *Fourier Transform Ion Mobility Spectrometry of Barbiturates After Capillary Gas Chromatography*, J. High Res. Chrom. Chrom. Commun. 9, 44-48 (1986); R. H. St. Louis, W. F. Siems, and H. H. Hill Jr., *Apodization Functions in Fourier Transform Ion Mobility Spectrometry*, Anal. Chem. 64, 171-177 (1992); Y.-H. Chen, W. F. Siems, and H. H. Hill Jr., *Fourier Transform Electrospray Ion Mobility Spectrometry*, Anal. Chim. Acta 334, 75-84 (1996); U.S. Pat. No. 4,633,083 to Knorr, et al.]. Franzen later described fast-FT and fast-HT multiplexing of IM by modulating the ion beam admittance to the drift cell by means of a Bradbury-Nielsen gate [U.S. Pat. No. 5,719,392 to Franzen]. A unique means for performing FT-IMS was also described by Tarver and Siems, whereby a frequency-domain spectrum is obtained by either frequency-sweeping a Bradbury-Nielsen gate and/or frequency-sweeping the detector signal using a fast commutator [U.S. Pat. No. 6,580,068 to Tarver, et al.]. In these different multiplexed IMS experiments it is taught that, by means of their implementation, the duty cycle is only optimally increased to approximately 50%.

Knorr has also described Fourier transform-TOFMS [U.S. Pat. No. 4,707,602 to Knorr]. The FT-TOFMS was equipped with an electron impact ionization source and provided a 25-fold increase in sensitivity over conventional signal-averaging [F. J. Knorr, M. Ajami, and D. A. Chatfield, *Fourier Transform Time-of-Flight Mass Spectrometry*, Anal. Chem. 58, 690-694 (1986)]. Zare and coworkers have described Hadamard transform-TOFMS to improve the instrumental duty cycle to nearly 50% by using a modulated continuous ESI ion beam with an 8191-order Hadamard matrix [A. Brock, N. Rodriguez, and R. N. Zare, *Hadamard Transform Time-of-Flight Mass Spectrometry*, Anal. Chem. 70, 3735-3741 (1998); A. Brock, N. Rodriguez, and R. N. Zare, *Characterization of a Hadamard Transform Time-of-Flight Mass Spectrometer*, Rev. Sci. Inst. 71, 1306-1318 (2000); F. M. Fernandez, J. M. Vadillo, J. R. Kimmel, M. Wetterhall, K. Markides, N. Rodriguez, and R. N. Zare, *Hadamard Transform Time-of-Flight Mass Spectrometry: A High-Speed Detector for Capillary-Format Separations*, Anal. Chem. 74, 1611-1617 (2002); R. N. Zare, F. M. Fernandez, and J. R. Kimmel, *Hadamard Transform Time-of-Flight Mass Spectrometry: More Signal, More of the Time*, Angew. Chem. Int. Ed. 42, 30-35 (2003); U.S. Pat. No. 6,300,626 to Brock, et al.]. Zare and colleagues have suggested the possibility of attaining ca. 100% duty cycle by electrostatic steering to modulate and direct the ion beam to different regions of a position sensitive detector [R. N. Zare, F. M. Fernandez, and J. R. Kimmel, *Hadamard Transform Time-of-Flight Mass Spectrometry: More Signal, More of the Time*, Angew. Chem. Int. Ed. 42, 30-35 (2003).]. Independently, Dowell suggested modulating the ion beam by switching between two sources, or by alternatively modulating a single beam by electrostatic steering and utilizing two detectors [U.S. Pat. No. 5,331,158 to Dowell]. Note that steering modulation in TOFMS dates back to 1948 [A. E. Cameron and D. F. Eggers Jr., Ion "Velocitron," Rev. Sci. Instrum. 19, 605-607 (1948)], but theoretical and practical implementation was not described until the early 1970s by Bakker [J. M. B. Bakker, *A Beam-Modulated Time-of-Flight Mass Spectrometer Part I: Theoretical Considerations*, J. Phys. E: Sci. Instrum. 6, 785-789 (1973); J. M. B. Bakker, *A Beam-Modulated Time-of-Flight Mass Spectrometer Part II: Experimental Work*, J. Phys. E: Sci. Instrum. 7, 364-368 (1974).]. In contrast to FT and HT modes of multiplexing TOFMS, Myerholtz and colleagues have described a technique based on bunching and overlapping ion packets in the field-free drift region and demodulating the resultant signal by using correlation algorithms to improve TOFMS duty cycle to ca. 50% [U.S. Pat. No. 5,396,065 to Myerholtz, et al.].

The present invention differs from the one-dimensional prior art (i.e., IMS or TOFMS) in that significant gains in sensitivity, throughput, and S/N are obtained by two-dimensions of time dispersive analyte ion separation, i.e., by coupling ion mobility-TOFMS and operating both dispersive dimensions in a multiplex data acquisition mode described herein.

BRIEF SUMMARY OF THE INVENTION

This invention describes a method for multiplexed data acquisition for gas-phase ion mobility coupled with mass spectrometry. The following brief summary more readily describes embodiments of the invention.

In one aspect of the present invention, there is a method for the acquisition of analytical data for a sample comprising the steps of generating packets of gas-phase ions and neutral species from the sample; introducing the packets into a time dispersive ion mobility drift cell at a rate faster than the transient rate of separation of the ions by the drift cell; separating the ions in a first dimension according to their ion mobility; sampling the ions eluted by the ion mobility drift cell into a mass spectrometer; separating the ions in a second dimension in the mass spectrometer; detecting a mass spectrometric signal for the ions; and, processing the mass spectrometric signal using the ion packet injection frequency and an ion mobility-mass-to-charge correlation function. Preferably, the step of generating comprises generating packets of gas-phase ions and neutral species using a source selected from the group consisting of laser desorption/ionization, electrospray, desorption electrospray ionization, nanospray, ion spray, photoionization, multiphoton ionization, resonance ionization, thermal ionization, surface ionization, electric field ionization, chemical ionization, atmospheric pressure chemical ionization, radioactive ionization, discharge arc/spark ionization, laser induced breakdown ionization, inductively coupled plasma ionization, direct current plasma ionization, capacitively coupled plasma ionization, glow discharge ionization, microwave plasma ionization, and any combination thereof. Where laser desorption/ionization is used, it may be one or more of atmospheric pressure MALDI, ultraviolet MALDI, infrared MALDI, direct LDI, surface enhanced laser/desorption ionization, and any combination thereof. In some embodiments, the step of generating packets of gas-phase ions and neutral species comprises generating packets of gas-phase ions and neutral species from spatially distinct regions of a surface that is selected from the group consisting of steel, gold, silver, copper, glass, polymers, silicon, self-assembled monolayers, nitrocellulose, condensed-phase substrates, chemically functional moieties, chemically reactive moieties, biomolecules, and any combination thereof. When biomolecules are analyzed, the biomolecules may be selected from the group consisting of proteins, nucleic acids, arrays thereof, patterns thereof, and layers thereof. In some embodiments, the polymers are selected from the group consisting of poly(dimethylsiloxane), elastomers, plastics, and teflon. Preferably, the step of separating ions in a first dimension comprises separating ions in an electric field selected from the group consisting of uniform electrostatic fields, periodic-focusing electrostatic fields, non-uniform electrostatic fields, traveling wave electrostatic fields, radiofrequency electrostatic fields, and any combination thereof. In some embodiments, the step of separating ions in a first dimension comprises separating ions by time dispersion on the basis of ion mobility, the ion mobility selected from the group consisting of low-field mobility, high-field mobility, and any combination thereof. Preferably, the step of separating ions in a first dimension comprises separating ions by collisions with one or more gases. In embodiments wherein the step of separating ions in a first dimension comprises separating ions by collisions with one or more gases, preferably the one or more gases is selected from the group consisting of helium, neon, argon, krypton, xenon, nitrogen, oxygen, methane, carbon dioxide, water, methanol, methyl fluoride, ammonia, deuterated analogs thereof, tritiated analogs thereof, and any combination thereof. In embodiments wherein the step of separating ions in a first dimension comprises separating ions by collisions with one or more gases, the collisions are preferably selected from the group consisting of reactive collisions, non-reactive collisions, and any combination thereof. In some embodiments, the step of separating the ions in a second dimension comprises separating the ions using a method selected from the group consisting of time-of-flight mass spectrometry, magnetic-sector mass spectrometry, electrostatic-sector mass spectrometry, double-focusing sector-field mass spectrometry, quadrupole mass spectrometry, ion trap mass spectrometry, ion cyclotron resonance mass spectrometry, accelerator mass spectrometry, orbitrap mass spectrometry, and any combination thereof. In some embodiments, the ions are further encoded in the second dimension using multiplex frequency-domain analysis techniques or weighing design techniques or both; and, decoded by application of a Fourier transform or Hadamard transform or both. In some embodiments, the step of introducing comprises introducing a plurality of packets at a plurality of energies. In some embodiments, the packets are introduced into the ion mobility drift cell under varying conditions, with the varying conditions comprising different experimental parameters for separation and wherein one or more of the ion packets are encoded by the frequency of introduction of the one or more ion packets. In some embodiments wherein the packets are introduced into the ion mobility drift cell under varying conditions comprising different experimental parameters, preferably the experimental parameters are selected from the group consisting of drift cell voltage, drift cell gas pressure, temperature, identity of drift cell gases, and any combination thereof. In some embodiments, the ions comprise ions of single atoms and ions of molecules. Typically wherein ions of molecules are analyzed, the molecules are selected from the group consisting of molecules possessing a molecular weight less than 500 amu; molecules possessing a molecular weight less than 10,000 amu; molecules possessing a molecular weight less than 100,000 amu; molecules possessing a molecular weight greater than 100,000 amu; and, any combination thereof. In some embodiments, the method further comprises forming a plurality of beams of gaseous ions and neutral species from the packets, and wherein the step of introducing comprises introducing the plurality of beams into a plurality of ion mobility drift tubes to form a plurality of mobility-separated beams. In some embodiments, the method further comprises introducing the plurality of mobility-separated beams into a plurality of CID (collision-induced dissociation) tubes. In some embodiments, the method further comprises introducing the plurality of mobility-separated beams through at least one RF ion guide. In some embodiments, the method further comprises introducing the plurality of mobility-separated beams into at least one mass spectrometer. Preferably, the mass spectrometer is a TOFMS. Preferably, the TOFMS comprises a position sensitive detector. In some embodiments, the method further comprises the steps of segregating the mass spectrometric signal corresponding to the output of a ion mobility channel. The plurality of beams may be formed from a single region on the sample, or may be formed from a plurality of regions on the sample. In some embodiments, the method further comprises ionizing the gas phase neutral species.

In another aspect of the present invention, there is a method for the acquisition of analytical data for a sample comprising the steps of generating packets of gas-phase ions and neutral species from said sample; introducing said packets into a time dispersive ion mobility drift cell at a rate faster than the transient rate of separation of said ions by said drift cell; separating said ions in a first dimension according to their ion mobility; activating the ions as they elute from the ion mobility drift cell for dissociation into fragment ions; sampling the ions eluted by the ion mobility drift cell into a mass spectrometer; separating said ions in a second dimension in said mass spectrometer; detecting a mass spectrometric signal for the ions; and, processing said mass spectrometric signal using the ion packet injection frequency and an ion mobility-mass-to-charge correlation function. Preferably, the step of generating comprises generating packets of gas-phase ions and neutral species using a source selected from the group consisting of laser desorption/ionization, electrospray, desorption electrospray ionization, nanospray, ion spray, photoionization, multiphoton ionization, resonance ionization, thermal ionization, surface ionization, electric field ionization, chemical ionization, atmospheric pressure chemical ionization, radioactive ionization, discharge arc/spark ionization, laser induced breakdown ionization, inductively coupled plasma ionization, direct current plasma ionization, capacitively coupled plasma ionization, glow discharge ionization, microwave plasma ionization, and any combination thereof. Where laser desorption/ionization is used, it may be one or more of atmospheric pressure MALDI, ultraviolet MALDI, infrared MALDI, direct LDI, surface enhanced laser/desorption ionization, and any combination thereof. In some embodiments, the step of generating comprises generating packets of gas-phase ions and neutral species from spatially distinct regions of a surface that is selected from the group consisting of steel, gold, silver, copper, glass, polymers, silicon, self-assembled monolayers, nitrocellulose, condensed-phase substrates, chemically functional moieties, chemically reactive moieties, biomolecules, and any combination thereof. When biomolecules are analyzed, the biomolecules may be selected from the group consisting of proteins, nucleic acids, arrays thereof, patterns thereof, and layers thereof. In some embodiments, the polymers are selected from the group consisting of poly(dimethylsiloxane), elastomers, plastics, teflon, and any combination thereof. Preferably, the step of separating ions in a first dimension comprises separating ions in an electric field selected from the group consisting of uniform electrostatic fields, periodic-focusing electrostatic fields, non-uniform electrostatic fields, traveling wave electrostatic fields, radiofrequency electrostatic fields, and any combination thereof. In some embodiments, the step of separating ions in a first dimension comprises separating ions by time dispersion on the basis of ion mobility, said ion mobility selected from the group consisting of low-field mobility, high-field mobility, and combinations thereof. Preferably, the step of separating ions in a first dimension comprises separating ions by collisions with one or more gases. In embodiments wherein the step of separating ions in a first dimension comprises separating ions by collisions with one or more gases, preferably the one or more gases is selected from the group consisting of helium, neon, argon, krypton, xenon, nitrogen, oxygen, methane, carbon dioxide, water, methanol, methyl fluoride, ammonia, deuterated analogs thereof, tritiated analogs thereof, and any combination thereof. In embodiments wherein the step of separating ions in a first dimension comprises separating ions by collisions with one or more gases, the collisions are selected from the group consisting of reactive collisions, non-reactive collisions, and any combination thereof. In some embodiments, the step of activating ions occurs prior to said step of separating said ions in said temporally-resolved mass spectrometer. In some embodiments, the step of activating ions as they elute from the ion mobility drift cell for dissociation into fragment ions comprises the use of a technique selected from the group consisting of collision induced dissociation, surface induced dissociation, photodissociation, multiphoton dissociation, resonance enhanced multiphoton dissociation, blackbody induced radiative dissociation, electron capture dissociation, electron transfer dissociation, and any combination thereof. In some embodiments, the step of separating said ions in a second dimension comprises separating said ions using a method selected from the group consisting of time-of-flight mass spectrometry, magnetic-sector mass spectrometry, electrostatic-sector mass spectrometry, double-focusing sector-field mass spectrometry, quadrupole mass spectrometry, ion trap mass spectrometry, ion cyclotron resonance mass spectrometry, accelerator mass spectrometry, orbitrap mass spectrometry, and any combination thereof. In some embodiments, the ions are further encoded in the second dimension using multiplex frequency-domain analysis techniques or weighing design techniques or both; and, decoded by application of a Fourier transform or Hadamard transform or both. Preferably, the step of introducing comprises introducing a plurality of packets at a plurality of energies. In some embodiments, multiple ion packets are introduced into the ion mobility drift cell under varying conditions, the varying conditions comprising different experimental parameters for separation and wherein one or more of said ion packets are encoded by the frequency of introduction of said one or more ion packets. In some embodiments wherein multiple ion packets are introduced into the ion mobility drift cell under varying conditions comprising different experimental parameters for separation, the experimental parameters are preferably selected from the group consisting of drift cell voltage, drift cell gas pressure, and any combination thereof. In some embodiments, the ions comprise ions of single atoms and ions of molecules. In some embodiments, the molecules are selected from the group consisting of molecules possessing a molecular weight less than 500 amu; molecules possessing a molecular weight less than 10,000 amu; molecules possessing a molecular weight less than 100,000 amu; molecules possessing a molecular weight greater than 100,000 amu; and, any combination thereof. In some embodiments, the method further comprises forming a plurality of beams of gaseous ions and neutral species from said packets, and wherein said step of introducing comprises introducing said plurality of beams into a plurality of ion mobility drift tubes to form a plurality of mobility-separated beams. In some embodiments, the method further comprises introducing the plurality of mobility-separated beams into a plurality of CID tubes. In some embodiments, the method further comprises introducing the plurality of mobility-separated beams through at least one RF ion guide. In some embodiments, the method further comprises introducing the plurality of mobility-separated beams into at least one mass spectrometer. Preferably, the mass spectrometer is a TOFMS. Preferably, the TOFMS comprises a position sensitive detector. In some embodiments, the method further comprises the step of segregating the mass spectrometric signal corresponding to the output of each ion mobility channel. The plurality of beams may be formed from a single region on the sample, or may be formed from a plurality of regions on the sample. In some embodiments, the method further comprises ionizing the gas phase neutral species.

In another aspect of the present invention, there is an apparatus for ion mobility-mass spectrometry comprising an ion source for generating ions; an ion mobility drift cell fluidly coupled to the ion source and receiving ions from the ion source; a first timing controller coupled to the ion source; a second timing controller coupled to the ion source; a temporally-resolving mass spectrometer fluidly coupled to the ion mobility drift cell, the mass spectrometer receiving ions from the ion mobility drift cell; and, a processor in communication with the ion source, the ion mobility drift cell, the first timing controller, the second timing controller, and the mass spectrometer. In some embodiments, the second timing controller is a burst-mode timing controller. In some embodiments, the ion source comprises an ion source selected from the group consisting of atmospheric pressure MALDI, ultraviolet MALDI, infrared MALDI, direct LDI, surface enhanced laser desorption/ionization, electrospray, desorption electrospray ionization, nanospray, ion spray, photoionization, multiphoton ionization, resonance ionization, thermal ionization, surface ionization, electric field ionization, chemical ionization, atmospheric pressure chemical ionization, radioactive ionization, discharge arc/spark ionization, laser induced breakdown ionization, inductively coupled plasma ionization, direct current plasma ionization, capacitively coupled plasma ionization, glow discharge ionization, microwave plasma ionization, and any combination thereof. In some embodiments, the ion mobility drift cell produces an electric field selected from the group consisting of uniform electrostatic fields, periodic-focusing electrostatic fields, non-uniform electrostatic fields, traveling wave electrostatic fields, radiofrequency electrostatic fields, and combinations thereof. In some embodiments, the ion mobility drift cell utilizes low-field mobility, high-field mobility, and any combination thereof. In some embodiments, the mass spectrometer is selected from the group consisting of a time-of-flight mass spectrometer, a magnetic-sector mass spectrometer, an electrostatic-sector mass spectrometer, a double-focusing sector-field mass spectrometer, a quadrupole mass spectrometer, an ion trap mass spectrometer, an ion cyclotron resonance mass spectrometer, an accelerator mass spectrometer, an orbitrap mass spectrometer, and any combination thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
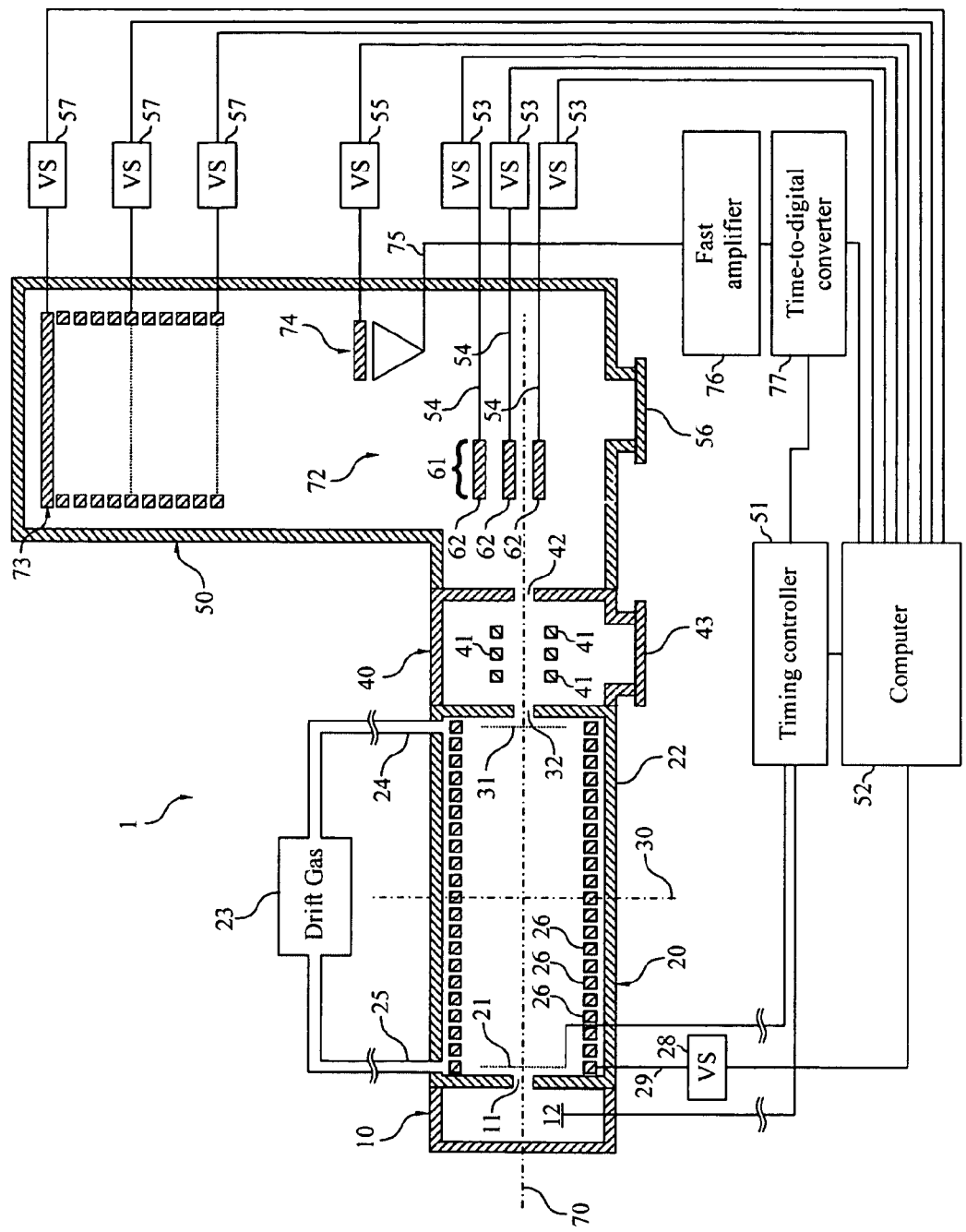
FIG. 1 is a schematic diagram of an ion mobility-time-of-flight mass spectrometer.

As used herein, "a" or "an" is defined herein as one or more. Unless otherwise indicated or apparent by the context, the singular includes the plural and the plural includes the singular herein.

As used herein, IM means ion mobility; MS means mass spectrometry when used in the context of a method and MS means mass spectrometer when used in the context of an apparatus; TOF means time-of-flight; TOFMS means time-of-flight mass spectrometry when used in the context of a method and TOFMS means time-of-flight mass spectrometer when used in the context of an apparatus.

As used herein, "mobility tube" is an ion mobility cell; the terms ion mobility cell and mobility tube are synonymous herein.

As used herein "collision induced dissociation tube" or "CID tube" is a tube in which high electric fields may be created sufficient to provide collision-induced dissociation of ions. In the present invention, the CID tube, when present can be used for collision-induced dissociation or alternatively, the collision-induced dissociation mode may be disabled and the CID tube may be used for cooling such as gas cooling and/or RF cooling.

Generally, an IM-TOFMS comprises generating packets of gas-phase ions from said sample, introducing the ion packets into a time dispersive ion mobility drift cell, separating the ions according to their ion mobility, sampling the ions eluted by the ion mobility drift cell into a temporally-resolving mass spectrometer, further separating said ions in said temporally-resolving mass spectrometer, and detecting a mass spectrometric signal for the ions. Preferably the separation axes of the ion mobility drift cell and that of the mass spectrometer are orthogonal.

Ion generation may be performed from any surface and from spatially distinct regions of a surface. These include, but are not limited to, surfaces of steel, gold, silver, copper, glass, polymers, self-assembled monolayers, nitrocellulose, condensed-phase substrates, chemically functional moieties, chemically reactive moieties, biologically active species, oligonucleotide arrays, protein arrays, aptamer arrays, antibody arrays, patterns and layers thereof, and any combination thereof. The polymers may be any polymers, with some non-limiting examples including poly(dimethylsiloxane), elastomers, plastics, teflon, and any combination thereof.

The first separation dimension in these methods is that of ion mobility. A variety of electric fields, known to those of skill in the art, may be used for this purpose. Electric fields used in this separation may be of any type, including, but not limited to, uniform electrostatic fields, periodic-focusing electrostatic fields, non-uniform electrostatic fields, traveling wave electrostatic fields, radiofrequency electrostatic fields, and any combination thereof. The ion mobility techniques used may be low-field mobility, high-field mobility, and any combination thereof. Drift tube gases used in this separation may be of any type, including, but not limited to, helium, neon, argon, krypton, xenon, nitrogen, oxygen, methane, carbon dioxide, water, methanol, methyl fluoride, ammonia, deuterated analogs thereof, tritiated analogs thereof, and any combination thereof. The drift tube gases aid in the separation by colliding with the species in the drift tube. These collisions may be reactive collisions, non-reactive collisions, and any combination thereof. The drift tube may have one or more gases.

The second separation dimension in these methods is that of mass spectrometry. The mass spectrometric technique employed in this regard may be any such technique, including, but not limited to, time-of-flight mass spectrometry, magnetic-sector mass spectrometry, electrostatic-sector mass spectrometry, double-focusing sector-field mass spectrometry, quadrupole mass spectrometry, ion trap mass spectrometry, ion cyclotron resonance mass spectrometry, accelerator mass spectrometry, orbitrap mass spectrometry, and any combination thereof.

An illustration of the major components of an ion mobility-time-of-flight mass spectrometer (IM-TOFMS) 1 is presented in FIG. 1. An IM-TOFMS instrument consists of five main components: a source of ions 10, an ion mobility drift chamber 20, a region after the drift chamber for collimating and focusing the ions eluting from the drift chamber 40, a time-of-flight mass spectrometer 50, and a computer 52 and associated electronics 51, 76, 77 for controlling the instrument.

Biological ions may be generated in the source by matrix assisted laser desorption/ionization (MALDI), electrospray (ESI), or nanospray. For one skilled in the art, it is clearly recognized that any means for generating ions proximal to the opening orifice 11 of the drift chamber 20 could be used. These include, but are not limited to, atmospheric pressure MALDI, ultraviolet MALDI, infrared MALDI, direct LDI (laser desorption ionization), surface enhanced laser desorption/ionization, electrospray, nanospray, ion spray, photoionization, multiphoton ionization, resonance ionization, thermal ionization, surface ionization, electric field ionization, chemical ionization, atmospheric pressure chemical ionization, radioactive ionization, discharge arc/spark ionization, laser induced breakdown ionization, inductively coupled plasma ionization, direct current plasma ionization, capacitively coupled plasma ionization, glow discharge ionization, microwave plasma ionization, and any combination thereof. The ion source region can further be operated at reduced pressure (<760 Torr) or at elevated pressure (>760 Torr) with means for transporting the ions from their point of inception to the plane of the drift chamber opening 11. A timing controller 51 provides a means for injecting ions into the drift chamber in a time-controlled manner. This is necessary to define $t_0$ in the ion mobility arrival time distribution and to for the mass spectrum [U.S. Pat. No. 6,683,299 to Fuhrer, et al.]. Timing-control of the ion beam is accomplished by using an intrinsically pulsed-source of ions as produced by MALDI, or by modulating a continuous ion beam (e.g., ESI) for admittance vs. no-admittance into the drift chamber, for example, by means of a mechanical chopper or electrostatic gate 21. Alternatively, a means for storing ions and injecting them in discrete intervals such as with a pulsed ion funnel [T. Wyttenbach, P. R. Kemper, and M. T. Bowers, *Design of a New Electrospray Ion Mobility Mass Spectrometer*, Int. J. Mass Spectrom. 212, 13-23 (2001)] or a pulsed ion trap (U.S. Pat. No. 6,559,441 to Clemmer) can be used.

The drift chamber 20 consists of a housing 22 in which the pressure can be accurately controlled by a metered drift gas supply 23 which delivers drift gas to the drift chamber proximal to the exit of the chamber 24 or the entrance of the chamber 25. Inside of the drift chamber housing 22, there consists a plurality of conductive elements 26 which are linked to one another by a series of resistive elements (not shown). By application of a potential from a voltage supply 28 via 29, the plurality of conductive elements 26 serves to generate an electric-field. In the prior art the electric-field thus formed is uniform across the longitudinal axis 70 of the drift chamber. It is recognized that alternate geometries of the conductive elements, or non-uniform valued resistive elements, can be utilized for generating non-uniform fields (U.S. Pat. No. 6,639,213 to Gillig, et al.). The drift chamber is terminated in an exit plane defined by an electrostatically controlled ion gate 31, or an exit orifice 32, for transmitting the ions eluting from the drift chamber to an ion optics region 40.

The ion optics region 40 is used for collimating and focusing the ions eluting from the drift chamber 20 by means of electrostatic or magnetic field ion optical elements 41. Those skilled in the art recognize that these elements can consist of a variety of geometries or combinations thereof for the purposes of ion beam collimation and focusing. This region can be further delineated by an exit aperture for purposes of creating a conductance limit and by reducing the gas number density by means of vacuum pumping 43. The ion beam is then transmitted in this conditioned state to the source 61 of a time-of-flight mass spectrometer 50. The TOFMS source consists of a series of electrostatically addressable plates and grids 62 (which comprise the source 61) for defining $t_0$ of the time-of-flight measurement. Potentials are applied to these plates and grids by means of voltage supplies 53 via connections 54. It is recognized by those skilled in the art that the number, spacing, potential, and specific time-domain waveform applied to the plates and grids can be varied for purposes of increasing ion transmission and/or time resolution in the time-of-flight measurement. Further, it is recognized that the orientation of the TOF source 61 relative to the longitudinal-axis of ion beam propagation 70 from the drift chamber can be varied. The orientation illustrated in the FIG. 1 is an orthogonal-time-of-flight 50, although a linear-time-of-flight could be used. In the orthogonal arrangement, ions are accelerated out of the TOF source into a field-free drift region 72, perpendicular (or nearly so) to the axis of their drift chamber translation 70. In the instrument of FIG. 1, the TOF drift region is capped by a reflectron 73 for purposes of kinetic energy focusing of the ion packet prior to striking electron multiplier multichannel plate 74 whereby the electron cascade is collected at the anode of the detector. Voltage supply 55 is connected to the multiplier multichannel plate 74; voltage supplies 57 are connected to the reflectron 73. This signal is transmitted via 75 to an amplifier 76 and subsequently to a time-to-digital converter 77 and computer 52 where it is registered and stored for processing. For one skilled in the art, it is recognized that other means for ion detection such as continuous dynode electron multipliers, Daly-type detectors, etc., can also be used with alternate means for collecting, storing, and processing the ion signal thus obtained.

Figure 2:
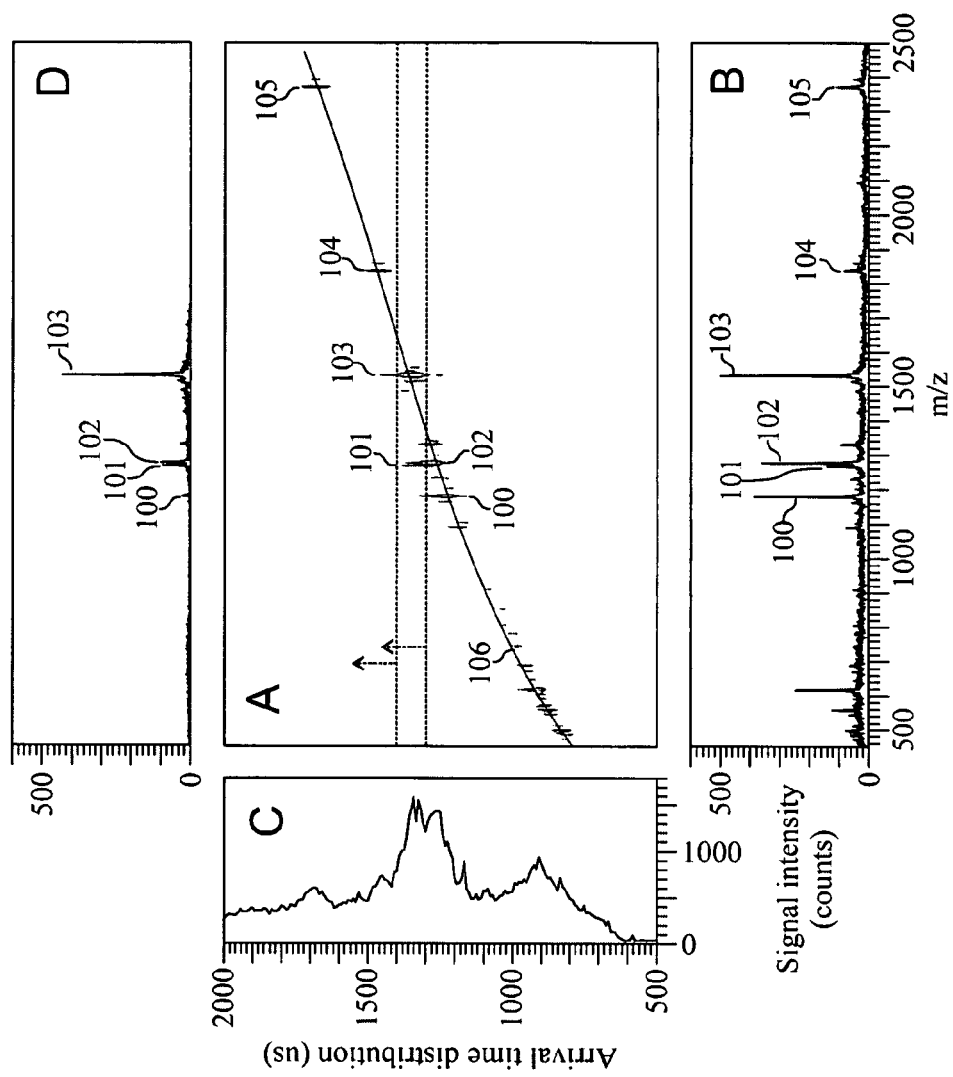
FIG. 2 is (A) A two dimensional-plot of arrival time distribution vs. mass-to-charge. (B) A plot of arrival time distribution integrated over all mass-to-charge space. (C) A plot of mass-to-charge integrated over all arrival time distribution space. (D) A plot of mass-to-charge integrated over the arrival time distribution range of 1300 to 1400 µs.

An example of the two-dimensional data obtained by using IM-TOFMS is illustrated in FIG. 2 for the peptides obtained from a proteolytic digest (tryptic) of bovine hemoglobin. The arrival time distribution (FIG. 2, left) is the signal that would be registered if the detector were placed at the exit plane of the drift chamber 32, that is, monitoring the one-dimensional ion mobility separation based primarily on the charge to collision cross-section of the ion. The arrival time distribution typically spans 0.1 to several 10 s of ms depending on the particular experimental arrangement. In contrast, the mass spectrometer disperses and detects the eluting ions over a duration of ca. 10-100 µs. Owing to the short timescale of the mass spectrometer analysis relative to that of the ion mobility, many mass spectra can be obtained over the course of the arrival time distribution to yield a two-dimensional plot like that shown in FIG. 2 (center). The resolution in the arrival time distribution can be improved by using interleaving data acquisition by means of post-processing or by using position sensitive detection (U.S. Pat. No. 6,683,299 to Fuhrer, et al.). By integrating the mass spectral signals over all arrival time distribution space, one obtains an integrated mass spectrum as illustrated in the bottom panel of FIG. 2. This is what would be obtained by performing mass spectrometry in the absence of ion mobility. However, by first dispersing the peptide signals (e.g., 100-105) by ion mobility, mass spectral congestion can be significantly reduced in the analysis of complex mixtures. The top panel in FIG. 2 illustrates the integrated mass spectrum obtained across arrival times of 1300-1400 µs (i.e., centered about the peptide signal 103 (VGGHAAEYGA-EALER, residues 17-31 of the bovine hemoglobin α-subunit)). Signals occurring outside this range are eliminated, i.e., chemical noise is significantly attenuated.

Also illustrated in FIG. 2 is that the ion signals arising for this mixture of peptides align in the two-dimensional spectrum in a highly predictable manner whereby ion signals for higher m/z analyte ions typically elute from the drift chamber at longer times than smaller m/z analyte ions. This is illustrated by the guideline 106, which is included to assist in visualizing this trend, which is hereafter termed a trendline. The trendline for a particular class of analytes (e.g., peptides) is a correlation function $f(t)$ relating the arrival time distribution to the m/z of an ion under particular ion mobility conditions. It is also apparent that greater than ca. 90% of the two-dimensional space does not, and is not expected to, contain analyte signals (i.e., regions above-left and below-right of the trendline 106), which ultimately represents inefficient sampling.

Figure 3:
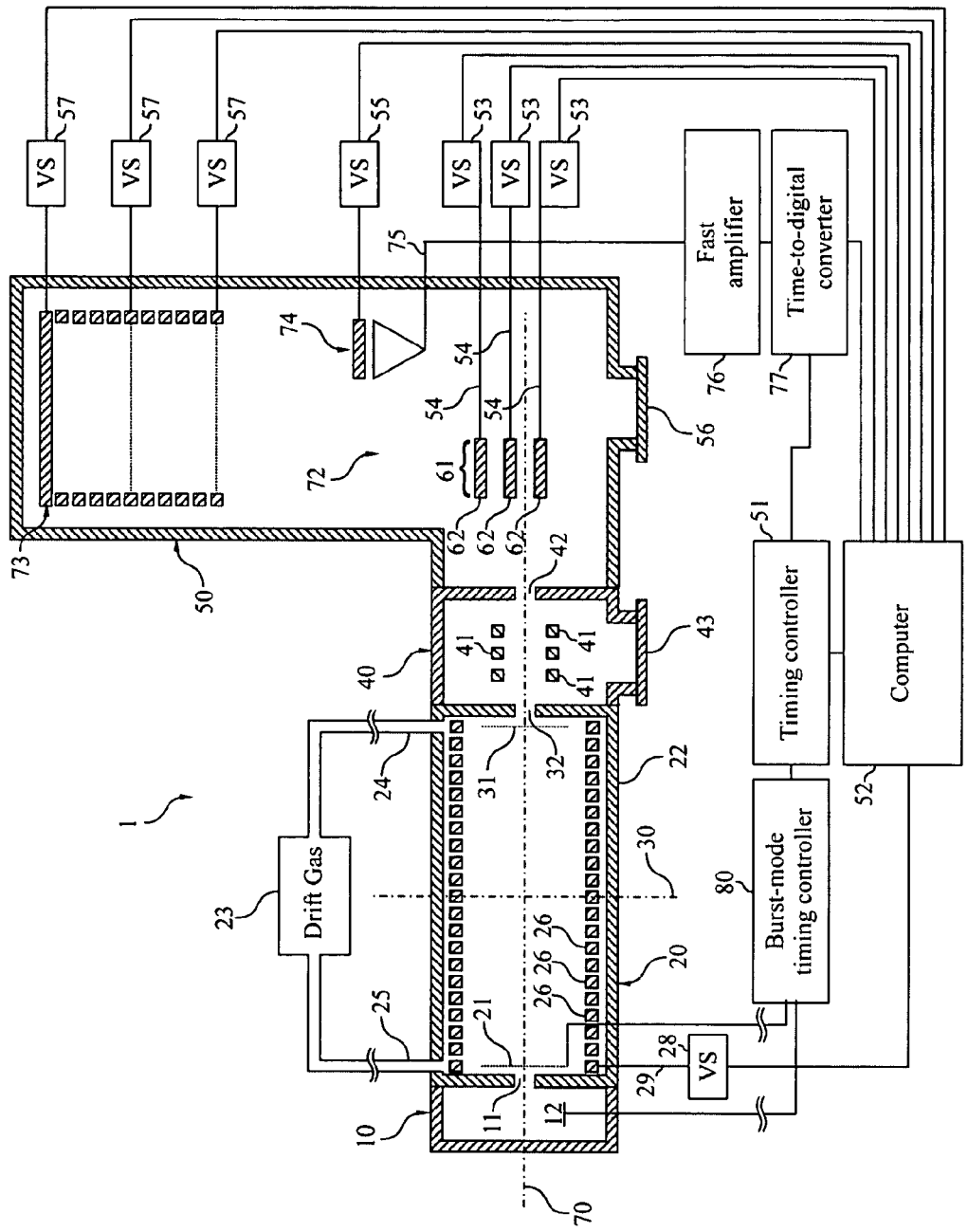
FIG. 3 is a schematic diagram of the preferred embodiment of the invention using an ion mobility-time-of-flight mass spectrometer.
Figure 4:
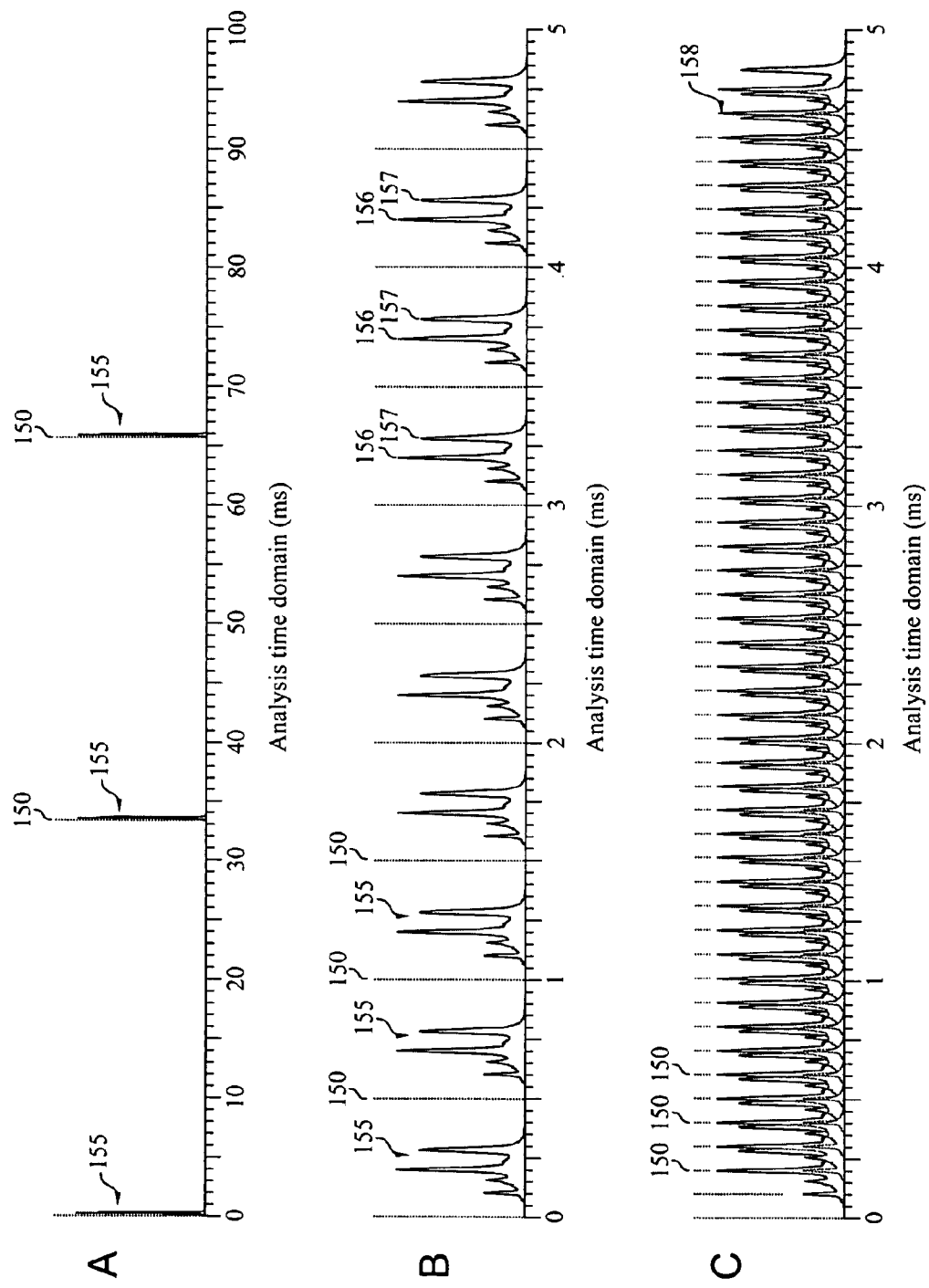
FIG. 4. (A) A diagram illustrating the typical timing sequence in IM-TOFMS, (B) a diagram illustrating a timing sequence representing 100% duty cycle, and (C) a diagram illustrating the preferred embodiment of the invention by injecting ions into the ion mobility chamber at a rate faster than the arrival time distribution.

This inefficiency and its consequences are addressed by the present invention. In the present invention, as illustrated in FIG. 3, a separate timing controller 80 is a burst mode timing controller and is triggered by the ion injection pulse of the prior art via 51. This second controller 80 is used to trigger a plurality of ion injection pulses for each sampling trigger (i.e., $t_o$). For example, FIG. 4A illustrates using MALDI at a repetition rate of 30 Hz (i.e., ion injection events 150 separated by 33.3 ms). The arrival time distribution for the peptides of a tryptic digest of horse heart cytochrome c 155, illustrate that the separation of these peptides is complete in ca. 500 μs. Other numerical indicators used in FIG. 3 are the same as those used in FIG. 1. In the FIG. 4A this represents an instrumental duty cycle of ca. 1.5%. The duty cycle approaches 100% when the time between ion injection events approaches the temporal extent of the arrival time distribution. For the purposes of this description, ion injection at a rate slower than or equal to the slowest eluting component will hereafter be termed sequential duty cycle. Ion injection at a rate faster than the slowest eluting component (i.e., time correlation for separate injection events is not apparent in one dimension, but rather frequency encoded) is hereafter termed multiplexed duty cycle. In embodiments of the present invention, packets of ions are introduced into a time dispersive ion mobility drift cell at a rate faster than the transient rate of ion packet separation. The concepts of sequential and multiplex duty cycle are illustrated in FIGS. 4B and 4C, respectively. FIG. 4B shows arrival time distributions of cytochrome c (simulated based on 155) where ion injection 150 is performed at a rate of 2 kHz (i.e., ion injection every 500 μs). Because this ion injection rate is commensurate with the duration of the arrival time distribution from the drift chamber, it represents essentially 100% sequential duty cycle. FIG. 4C illustrates the preferred embodiment of the invention whereby ion injection is performed at a rate faster than 100% sequential duty cycle for the drift chamber, i.e., 10 kHz in FIG. 4C. In this situation, the arrival time distributions are no longer discrete, which means that they cannot be simply summed or averaged as in the case of FIG. 4A or 4B. Rather, the signals for individual ion injections are phase-shifted dependent upon the ion mobility of the particular analyte. Owing to this phase-shift, the convoluted arrival time distribution 158 must be decoded/demodulated to recover the IM time correlation. In the preferred embodiment, the arrival time distribution is demodulated by means of a mass spectrometer. In some embodiments of present invention, the mass spectrometric signal is processed using the ion packet injection frequency and an ion mobility-mass-to-charge correlation function.

Along these lines multiple ion packets can be introduced into the ion mobility drift cell under varying conditions. These varying conditions may be different experimental parameters for separation. In this way, one or more of the ion packets are encoded by their frequency of introduction. Examples of such experimental parameters include, but are not limited to, drift cell voltage, drift cell gas pressure, temperature, identity of drift cell gases, and any combination thereof.

Figure 5A:
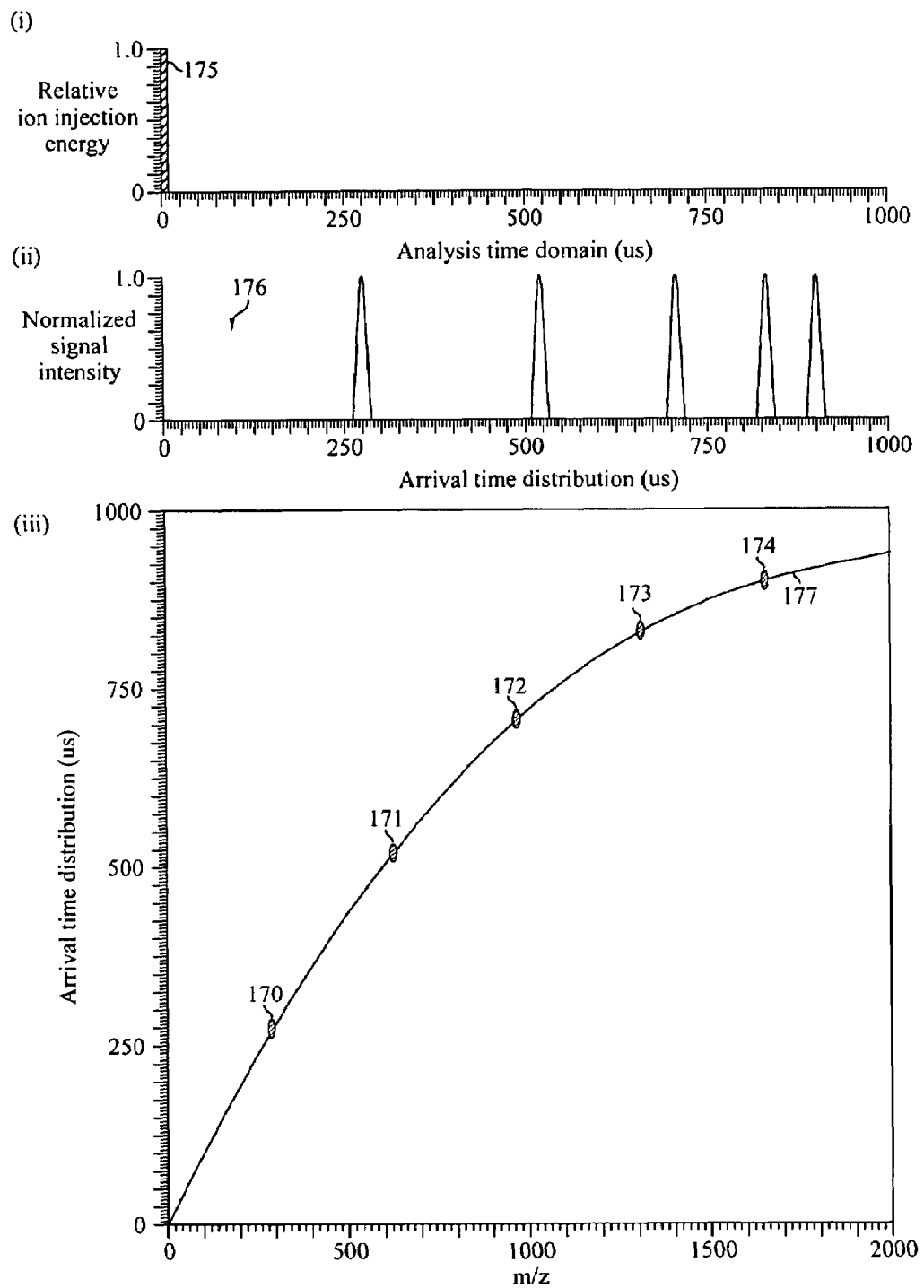
FIG. 5A. (i) A diagram illustrating the ion injection timing, (ii) a diagram illustrating the arrival time distribution in the ion mobility dimension for five hypothetical analyte peaks, and (iii) a two-dimensional plot of the arrival time distribution further separated by mass-to-charge for five hypothetical analytes.
Figure 5B:
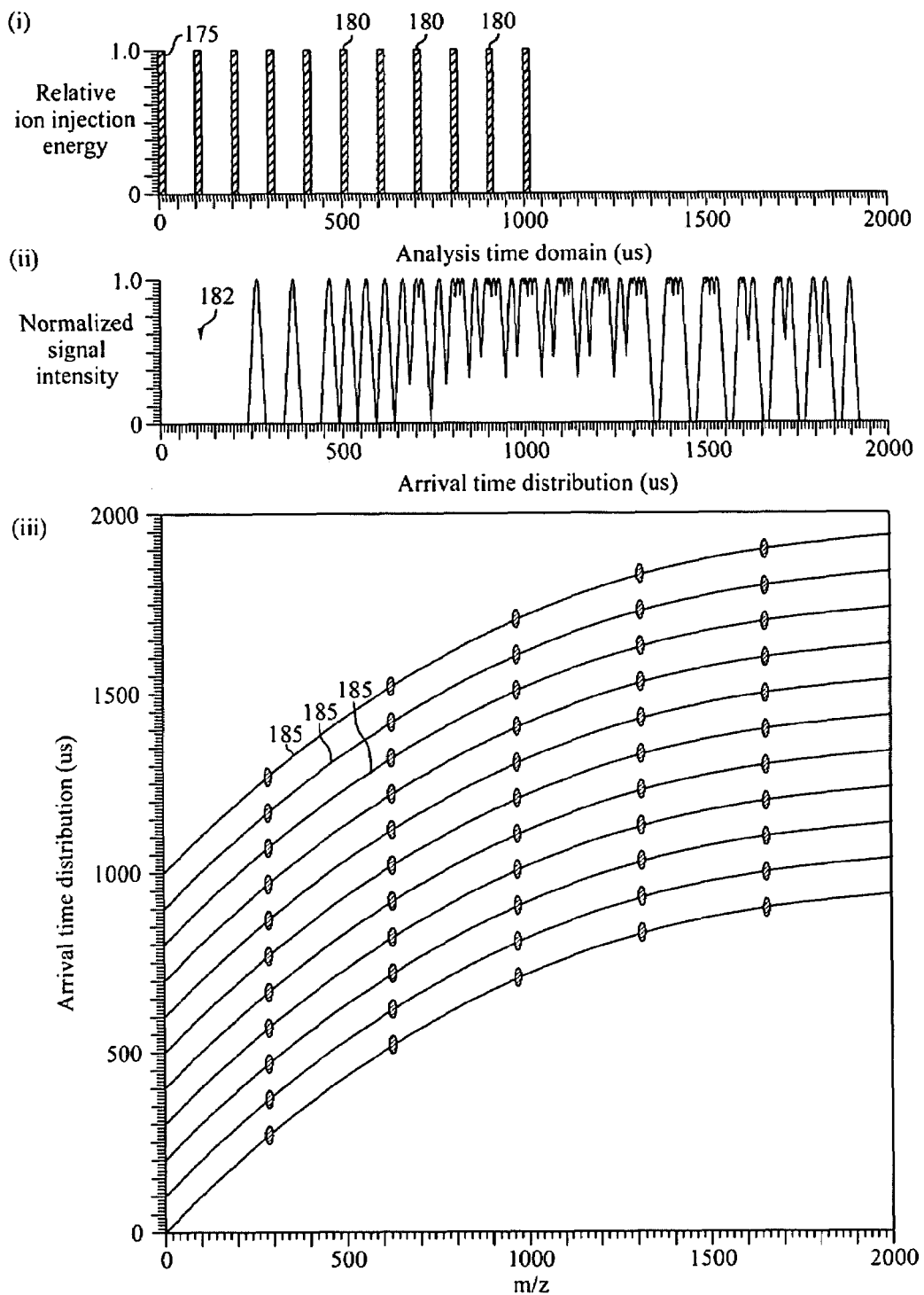
FIG. 5B. (i) A diagram illustrating the ion injection timing, (ii) a diagram illustrating the arrival time distribution in the ion mobility dimension for five hypothetical analyte peaks, and (iii) a two-dimensional plot of the arrival time distribution further separated by mass-to-charge for five hypothetical analytes in the preferred embodiment of the present invention.

FIG. 5 illustrates demodulation of the convoluted arrival time distribution. The analysis of a hypothetical five component 170-174 analyte mixture by using conventional IM-MS means is shown in FIG. 5A. In the analysis time domain (i), the single ion injection 175 produces an arrival time distribution 176 as shown in (ii), where signals fall along a trendline 177 (with correlation function $f(t)$) when subsequently sampled by mass spectrometry (iii). Again, note the large regions above-left and below-right of the trendline 177 which do not contain analyte signals. In the present invention, this sampling space is filled with analyte signal by operation in a multiplex-mode of ion injection. This is illustrated in FIG. 5B, where the initial ion injection 175 is followed thereafter with a series of 10 additional injections 180. This yields a plurality of ion packets in the drift chamber at the same time, but at different stages of ion separation (ii). When the convoluted arrival time distribution 182 is subsequently sampled by the mass spectrometer, the two-dimensional separation (iii) yields 11 trendlines 185 each offset from one another by Δt, which equals the temporal spacing between ion injections 180.

In this example, the arrival time distribution for separating the analytes of one ion packet/injection is ca. 1 ms. By injecting 10 additional ion packets each separated by 100 μs, the arrival time distribution dimension must be increased by a factor of 2 to fully accommodate the phase-shifted separations. However, there is a net factor of 5.5 increase in total ion signal detected when normalized to the total analysis time (i.e., 11 trendlines/2 times increase in sampling space). Ultimately, this signal intensity enhancement is limited by the highest multiplex-mode frequency that can be demodulated by the mass spectrometer (provided the total number of ions injected per pulse remain constant as a function of frequency). This frequency is determined by four complementary factors for the particular instrumental arrangement and conditions utilized: (i) resolution in the ion mobility dimension, (ii) resolution in the mass spectrometry dimension, (iii) time of elution for the lowest mobility analyte, and (iv) slope of the trendline. Typical values for the instrumentation presently used range from 20 to 100 for ion mobility resolution (t/Δt, full width at half maximum (FWHM)), 100 to 10,000 for TOFMS resolution (t/2Δt, FWHM), and 0.2 to 10 ms for the elution time of the lowest mobility analytes. Thus, examining two practical extremes, i.e., high mobility resolution (t/Δt=100)/short elution time (0.2 ms) and low mobility resolution (t/Δt=20)/long elution time (10 ms), yields a multiplex frequency upper limit in the range of 2 to 500 kHz (500 to 2 μs pulse separation). These limits are provided for illustrative purposes and future improvements in both instrumentation and separations would provide an even broader range of values. It should be noted that by using MALDI in the present embodiment, the pulse width of the ion injection at high multiplex frequency is not detrimental to IM resolution as it is defined by the laser pulse width (0.5 to 15 ns) which is a factor of ca. $10^3$ to $10^6$ faster than the multiplex-mode frequency limits outlined above.

Figure 6:
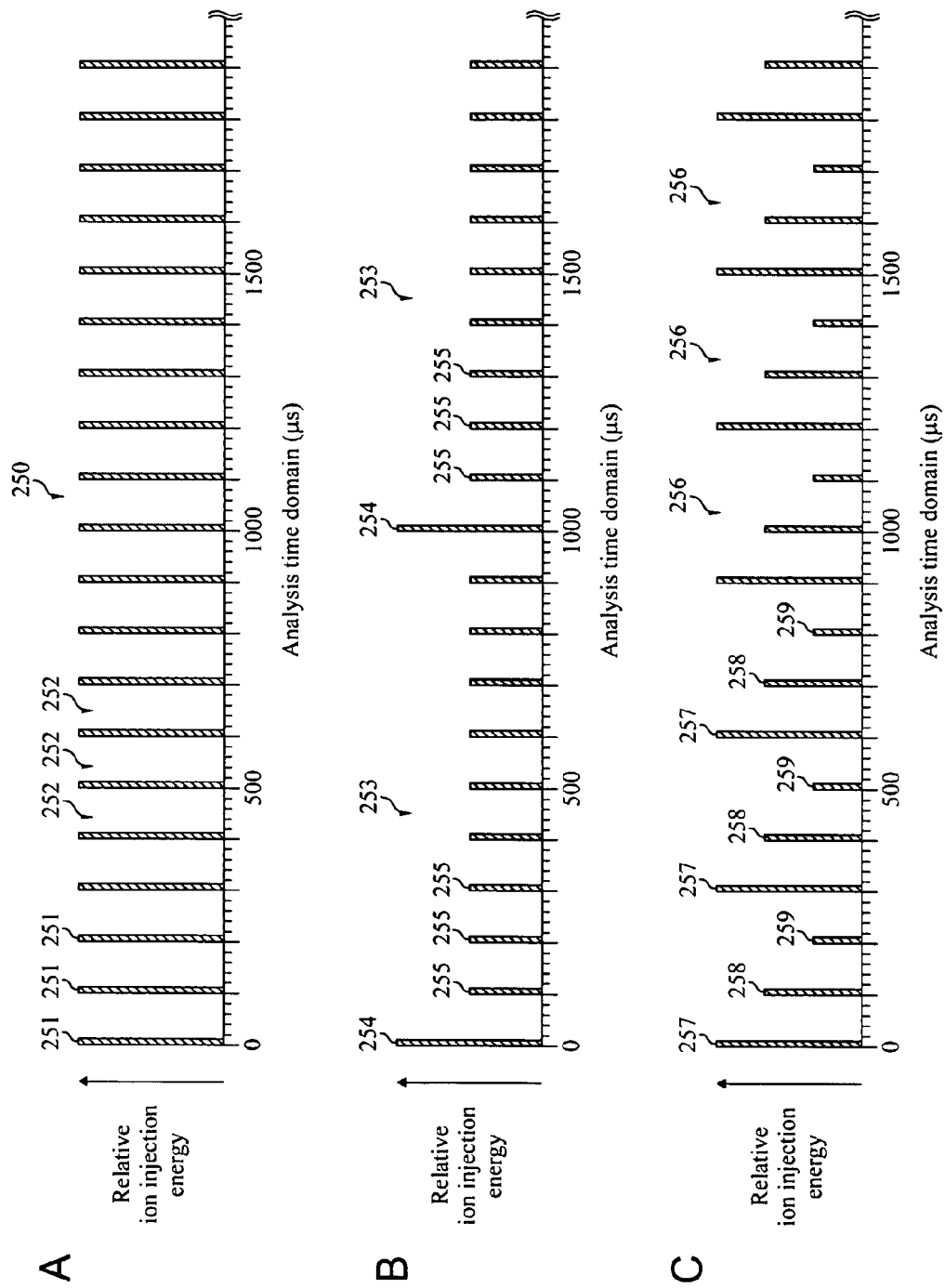
FIG. 6. Diagrams illustrating timing sequences for different modes of correlated data acquisition by IM-TOFMS. (A) Ion injection with constant relative ion injection energies. (B) Ion injection with alternating relative ion injection energies. (C) Ion injection by cycling of different relative ion injection energies.

In addition to varying the period of the multiplex-mode frequency 252 (FIG. 6), the relative ion injection energy of the pulse train 250 can also be varied at a second or additional frequencies to affect the number and types of ions injected. For example, FIG. 6A illustrates a constant relative ion energy multiplex-mode at a frequency of 10 kHz 251. In FIG. 6B, superimposed on the multiplex-mode frequency 255 is a 1 kHz injection frequency 254 of higher ion injection energy. By changing the relative ion injection energy (e.g., FIG. 6B) one can promote higher energy processes (e.g., in-source decay) at one frequency 254 and retain lower energy ionization conditions 255 at a second frequency. By using this approach, several spectra are obtained at different experimental conditions (e.g., 257-259 FIG. 6C), but in the same rapid multiplex-mode analysis.

Figure 7:
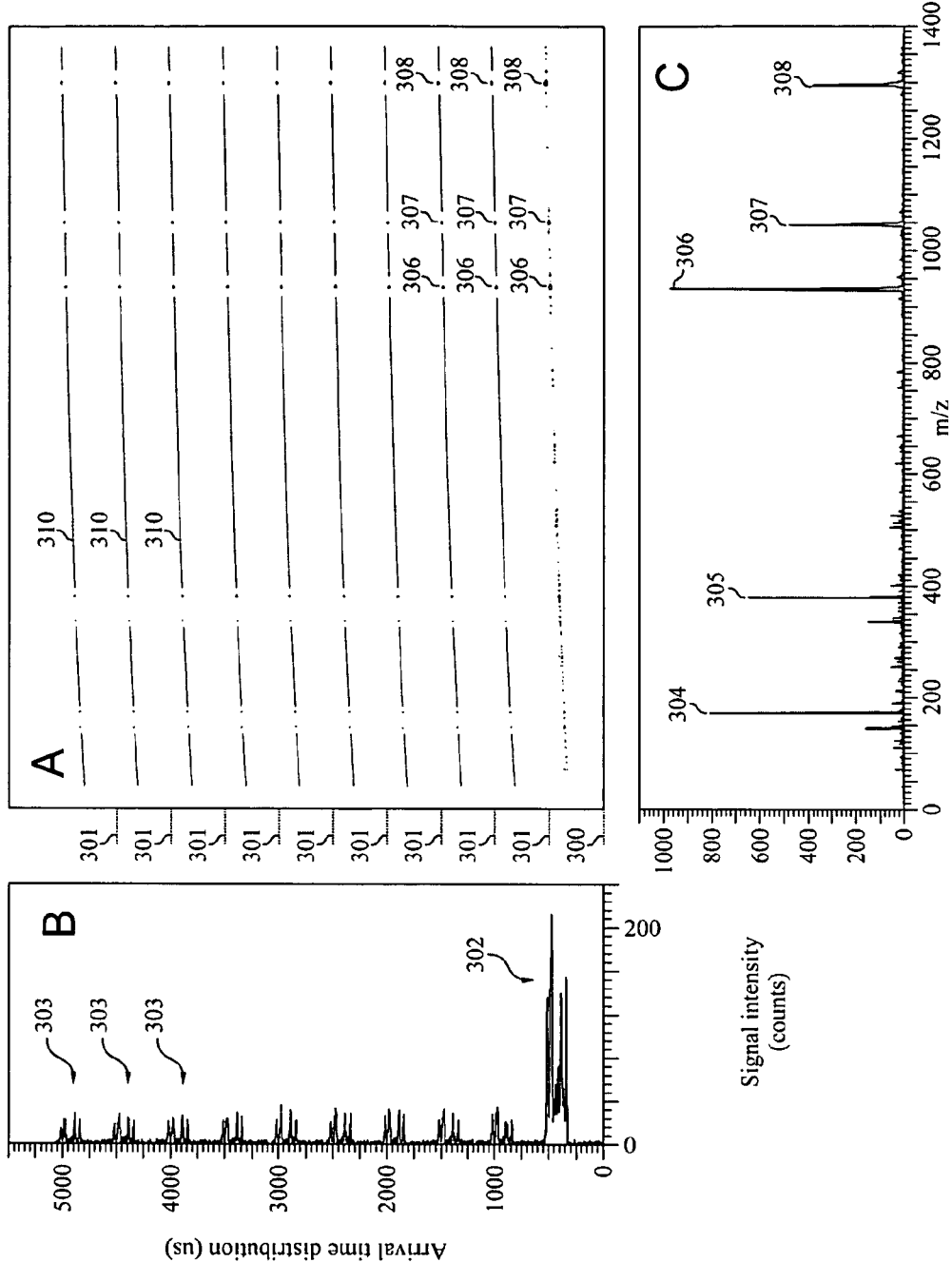
FIG. 7. (A) A two dimensional-plot of arrival time distribution vs. mass-to-charge using multiplex-mode ion injections (scheme (B) of FIG. 6) in the analysis of three peptides (angiotensin III (RVYIHPF, M.W.=930.52), angiotensin II (DRVYIHPF, M.W.=1045.54), and angiotensin I (DRVYIHPFHL, M. W.=1295.69). (B) A plot of arrival time distribution integrated over all mass-to-charge space. (C) A plot of mass-to-charge integrated over all arrival time distribution space. Guidelines 310 in the two-dimensional plot are to assist in visualizing the arrival time distribution-mass-to-charge correlation from each ion injection.

A demonstration of a preferred embodiment is illustrated in FIG. 7 for a mixture of 3 peptides: human angiotensin III 306 (RVYIHPF, M.W.=930.52), human angiotensin II 307 (DRVYIHPF, M.W.=1045.54), and human angiotensin I 308

Figure 8:
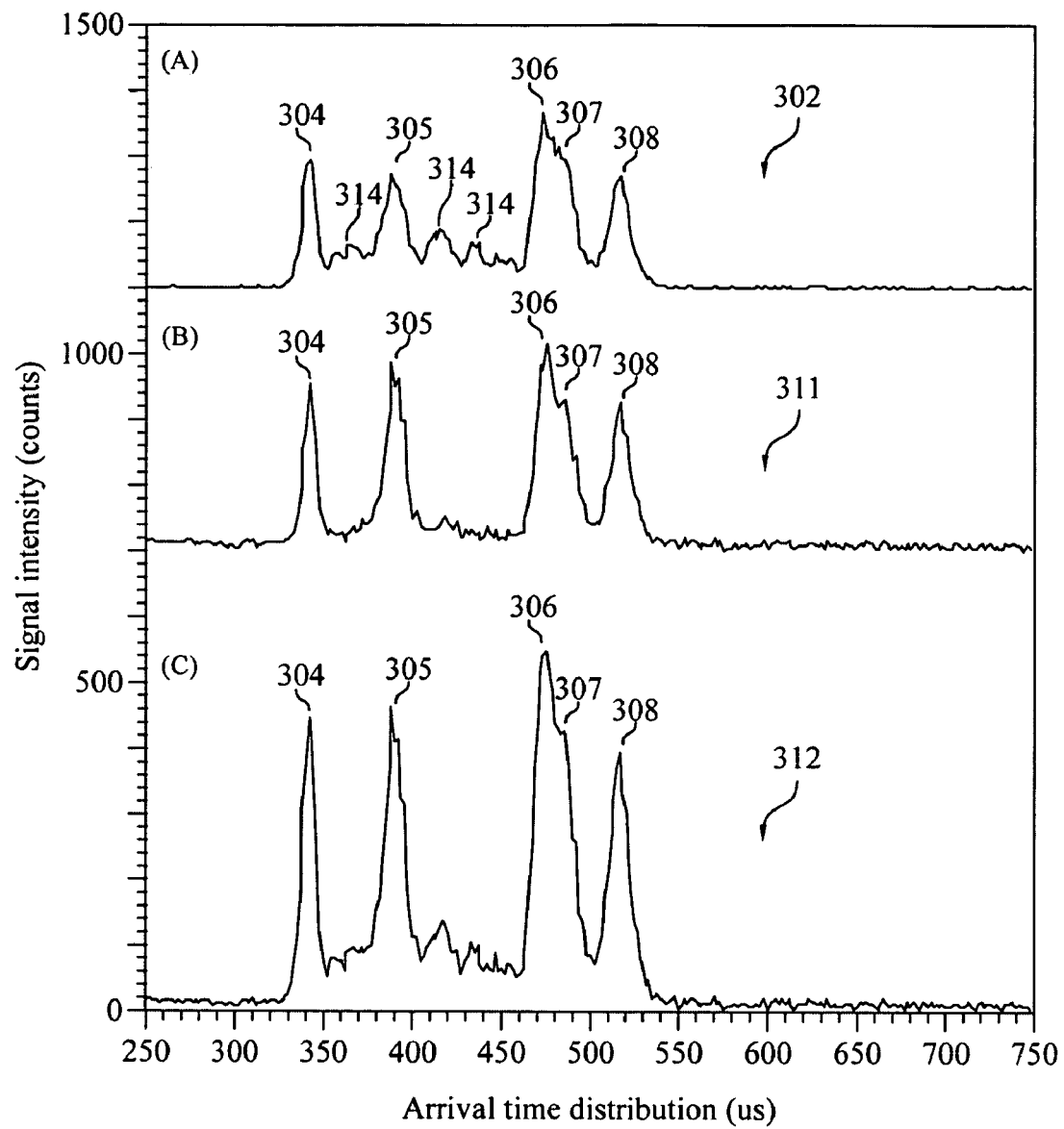
FIG. 8. Arrival time distributions for the data in FIG. 7 integrated over multiple ion injections. (A) The arrival time distribution obtained for the first ion injection (300, relatively high energy). (B) The arrival time distribution obtained by integrating the nine subsequent ion injections (301, relatively low energy). (C) The arrival time distribution obtained by integrating all ion injection events. Arrival time distribution plots (A) and (B) are offset for clarity.

(DRVYIHPFHL, M.W.=1295.69). MALDI was performed using α-cyano-4-hydroxycinnamic acid (CHCA, M.W.=189.16) giving rise to the additional matrix-derived signals of [CHCA+H]$^+$ 304 and to [2CHCA+H]$^+$ 305. In this analysis, the sampling cycle timing was initiated at a frequency of 150 Hz, whereby the first MALDI event 300 was performed at high relative energy (ca. 14.8 µJ pulse$^{-1}$) and 9 subsequent MALDI events 301 were performed at lower relative energy (ca. 9.1 µJ pulse$^{-1}$) at a frequency of 2000 Hz (500 µs ion injection separation). This is analogous to the timing scheme depicted in FIG. 6B. For each ion injection event, trendlines 310 are illustrated to assist in visualizing the data. The convoluted arrival time distribution is shown in FIG. 7B and the integrated mass spectrum (over all injections) is shown in FIG. 7C. The lower energy MALDI pulses 301 result in lower ion yields 303 than that at higher MALDI energies 302; however, the former provides softer ionization conditions, which reduces spectral complexity. For example, FIG. 8 illustrates the arrival time distributions obtained by integrating over the different energy multiplex-mode signals. FIG. 8A shows the expanded arrival time distribution of the higher energy pulse 302. In addition to peaks for the matrix 304,305 and protonated molecular peptide ions 306-308, several additional features are noted 314, which correspond to in-source decay fragment ions. These fragment ions are not observed by integrating the nine lower energy ion injection arrival time distributions 303 as illustrated in FIG. 7B. Further, the ion mobility resolution appears to be slightly improved over the higher MALDI energy ion injection (e.g., inspection of signals 306 and 307 in FIGS. 8A and B). Integrating signals for both high and low energy regimes provides enhanced sensitivity as shown in FIG. 8C. Thus, by modulating the relative energy for ionization/injection, particular ion species produced by different energy regimes can be selectively acquired in the same analysis.

Figure 9:
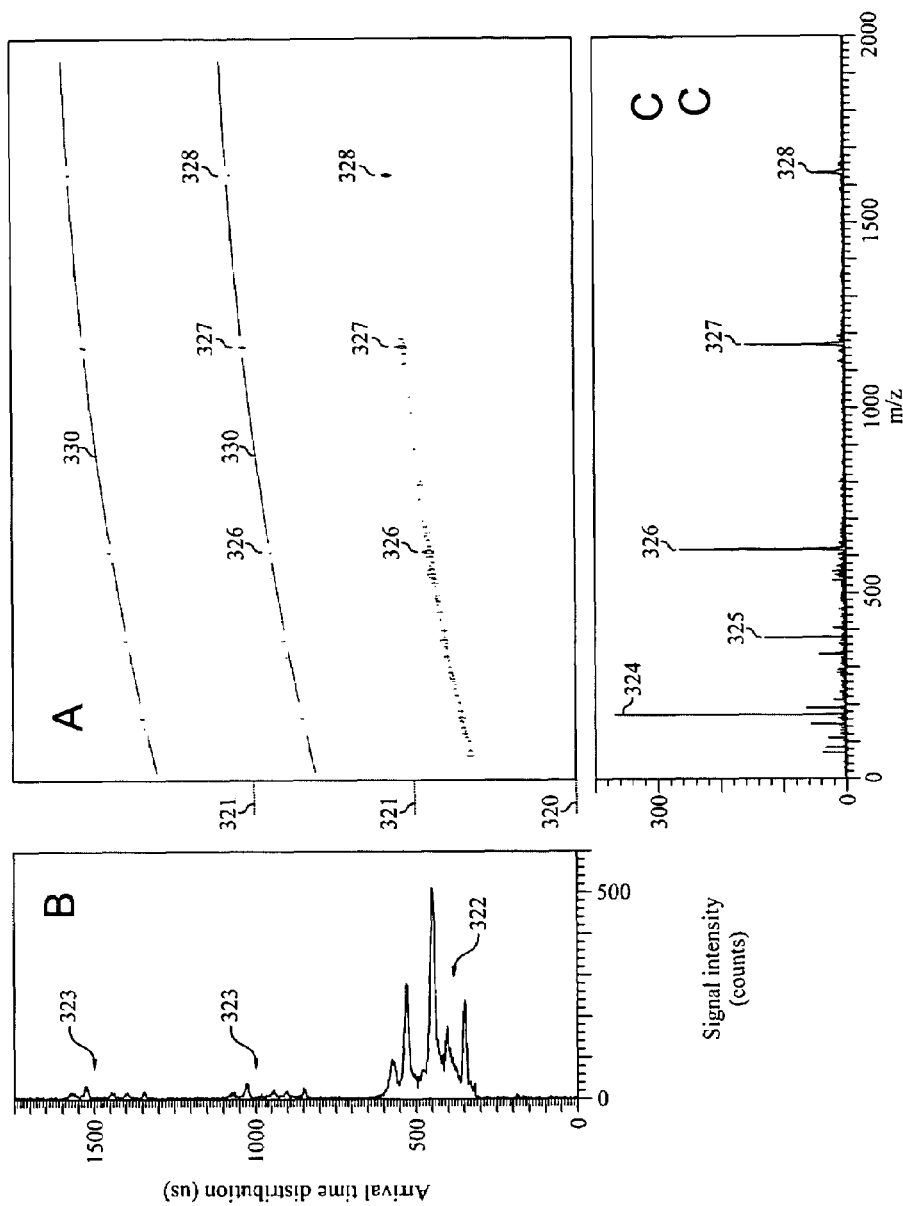
FIG. 9. (A) A two dimensional-plot of arrival time distribution vs. mass-to-charge using multiplex-mode ion injections (scheme (B) of FIG. 6) in the analysis of a tryptic digest of cytochrome c (horse heart). (B) A plot of arrival time distribution integrated over all mass-to-charge space. (C) A plot of mass-to-charge integrated over all arrival time distribution space; guidelines 330 in the two-dimensional plot are to assist in visualizing the arrival time distribution-mass-to-charge correlation from each ion injection.

FIG. 9 illustrates data for the multiplex-mode analysis of a tryptic digest of cytochrome c. The three analyte signals of highest abundance correspond to: the heme porphyrin group 326 ($C_{34}H_{30}O_4N_4Fe$, M.W.=616.18), TGPNLHGLFGR 327 (fragment 28-38, M.W.=1168.33), and CAQCHTVEK+heme 328 (fragment 14-22 including covalently attached heme (at positions $^{14}$Cys and $^{17}$Cys), M.W.=1634.36). MALDI was again performed using CHCA giving rise to the characteristic matrix-related signals 324 [CHCA+H]$^+$ and 325 [2CHCA+H]$^+$. The sampling cycle timing was initiated at a frequency of 150 Hz, whereby the first MALDI event 320 was performed at high relative energy (ca. 14.8 µJ pulse$^{-1}$) and 2 subsequent MALDI events 321 were performed at lower relative energy (ca. 9.1 µJ pulse$^{-1}$) at a frequency of 2000 Hz. For each ion injection event, trendlines 330 are indicated to assist in visualizing the data. Inspection of the integrated arrival time distributions for high 322 and low 323 relative energy ion injection events reveals significant differences in the relative abundance observed for the small molecule heme group 326, peptide 327, and peptide+ligand (heme) 328.

Figure 10:
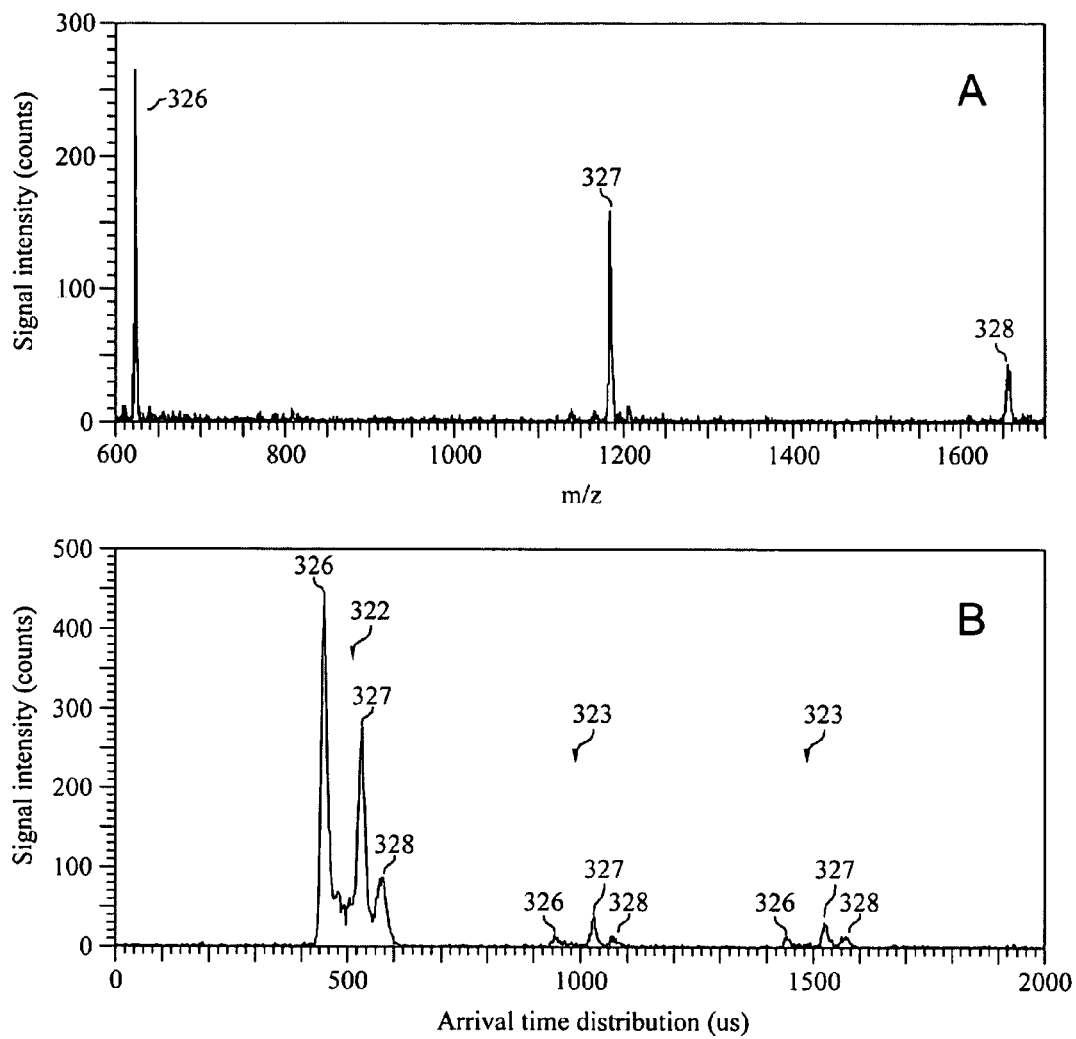
FIG. 10. (A) A plot of mass-to-charge integrated over all arrival time distribution space for the region of m/z 600-1200 for the data in FIG. 9. (B) The arrival time distribution obtained by integrating over the m/z region in (A).

To illustrate the differences in ion signals observed at both high and lower energy, FIG. 10 focuses on the region including heme 326, TGPNLHGLFGR 327, CAQCHTVEK+heme 328. The integrated mass spectrum for the mass range of m/z=600 to 1700 is presented in FIG. 10A, The integrated arrival time distribution for this mass range in multiplex-mode operation is illustrated in FIG. 10B. The wavelength used for MALDI in this analysis (349 nm, frequency-tripled Nd:YLF) corresponds closely with a resonant line in the Soret region of heme [G. Loew, *Structure, Spectra, and Function of Heme Sites*, Int. J. Quantum Chem. 77, 54-70 (2000)]. Thus, at higher ion injection energy, the relative abundance of heme 326 is significantly higher relative to lower ion injection energy, which better favors ionization and injection of intact peptide molecules (e.g., 327). For example, the abundance ratio of heme-to-peptide (326/327) is 1.57 and 0.41 for high energy and low energy injections, respectively. In contrast, the abundance ratio of peptide+heme-to-peptide (328/327) remains nearly constant regardless of injection energy (0.31 and 0.40 for high and low energies, respectively). This observation suggests that the small molecule-peptide complex exhibits ionization characteristics that resemble those for the peptide rather than the small molecule alone. By utilizing different energy regimes in the same multiplex-mode analysis, individual spectra representing these different ionization/injection conditions can be obtained nearly simultaneously.

Figure 11:
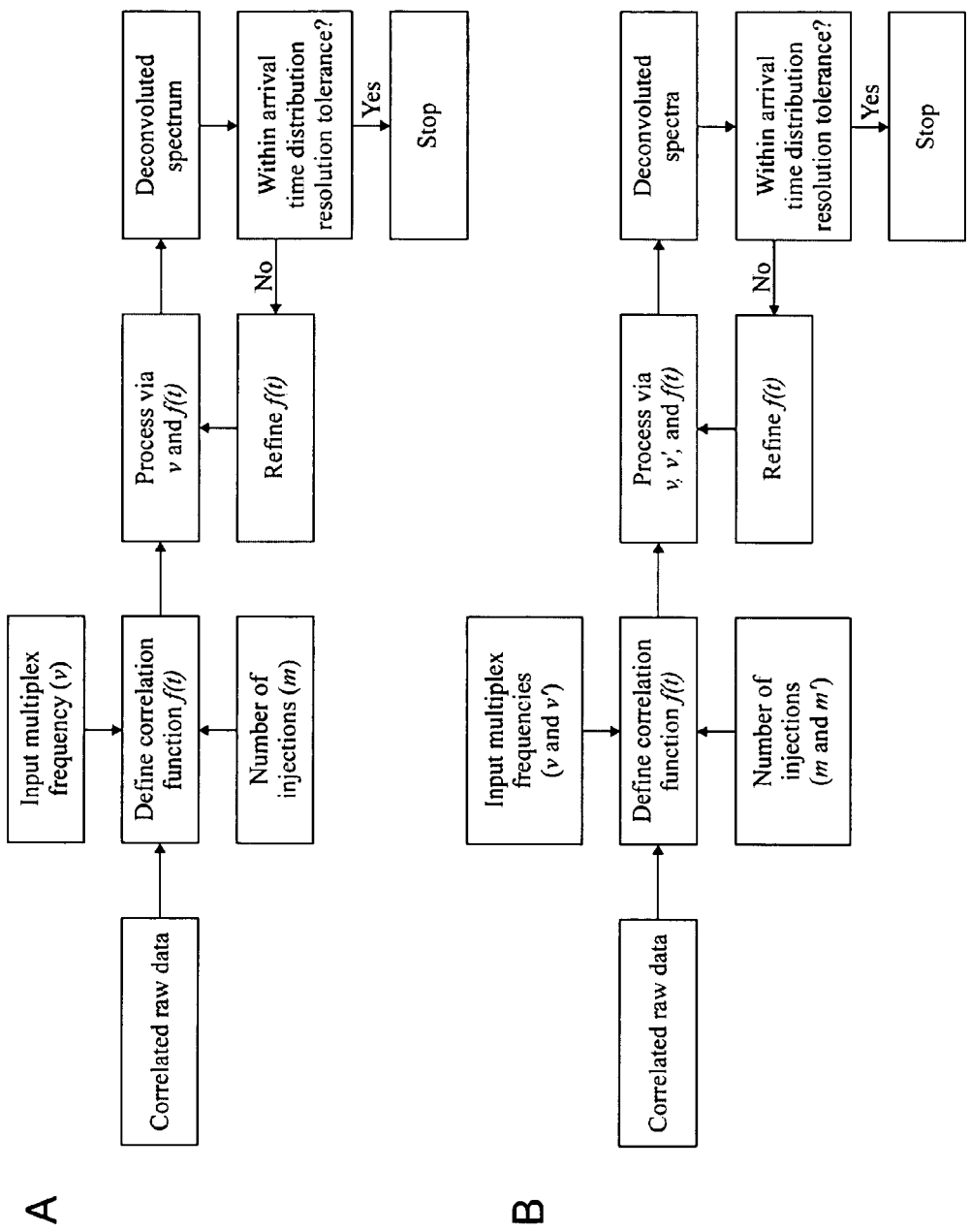
FIG. 11. (A) Post-processing scheme for deconvolution of the ion mobility arrival time distribution using a multiplex-mode with constant relative ion injection energies (e.g., see FIG. 6(A)). (B) Post-processing scheme for deconvolution of the ion mobility arrival time distribution using a multiplex-mode with alternating or cycling relative ion injection energies (e.g., see FIGS. 6B and 6C).

A schematic flowchart for processing of the multiplex data is presented in FIG. 11. In general, the correlated raw data is examined with the a priori knowledge of the multiplex-mode frequency (v, Δt) and the number of ion injections (m) (FIG. 11A). By selecting two or more points in a single trendline, the correlation function ($f(t)$) can be readily defined. Note that for a given gas number density (N) and electric field strength (E), $f(t)$ must only be determined once, because the slope of $f(t)$ does not vary considerably for a particular molecular class. Resolution in the arrival time distribution can be used as a convergence variable to ensure an appropriate estimate of $f(t)$ was made. The deconvoluted spectrum ($c_{ff}$) for equal energy ion injections (see e.g., FIG. 6(A)) is then obtained by:

$$c_{ff}(n\Delta t) = \sum_{n=0}^{m} f(t) f(t + n\Delta t) \quad n = 0, 1, 2 \ldots m$$

which sums the signals from each individual trendline. When two or more ion injection energies or multiplex frequencies (e.g., v', $\Delta t_1$ and v", $\Delta t_2$) are used (see e.g., FIG. 6B), the deconvoluted spectra are obtained by:

$$c_{ff1}(n\Delta t_1) = \sum_{n=0}^{m} f(t) f(t + n\Delta t_1) \quad n = 0, 1, 2 \ldots m$$

$$c_{ff2}(n\Delta t_2) = \sum_{n=0}^{m} f(t + \Delta t_2) f(t + n\Delta t_2) \quad n = 0, 1, 2 \ldots m$$

which is illustrated schematically in FIG. 11 (B). Note that this processing scheme readily scales with additional multiplex frequencies (i.e., >2).

Figure 12:
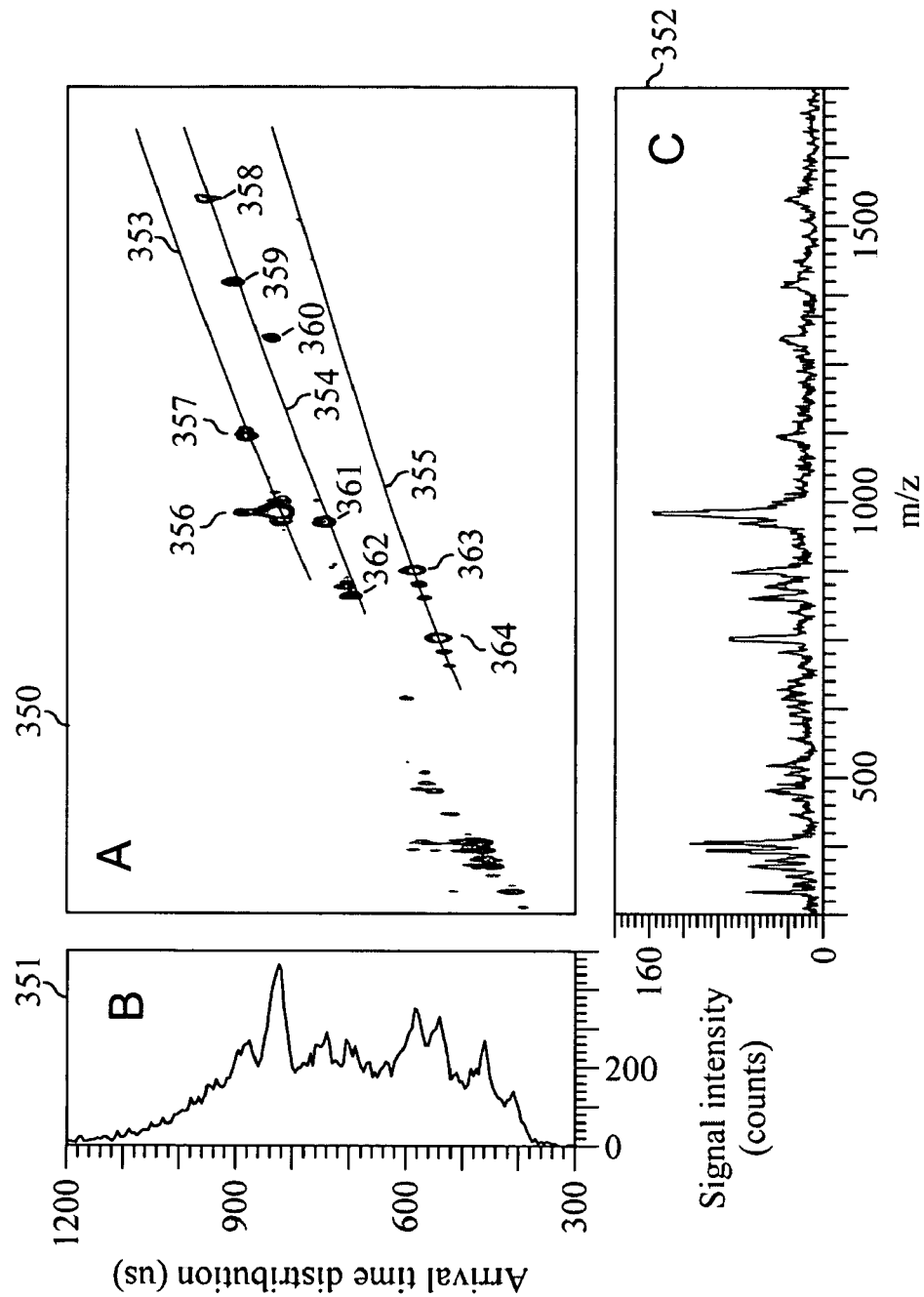
FIG. 12. A two-dimensional plot of arrival time distribution vs. mass-to-charge for analytes of different molecular classes (peptide, oligonucleotide, and carbon clusters). Guidelines 353-355 in the two-dimensional plot are to assist in visualizing the arrival time distribution-mass-to-charge correlation for each class. (B) A plot of arrival time distribution integrated over all mass-to-charge space. (C) A plot of mass-to-charge integrated over all arrival time distribution space.

In the analysis of complex materials (e.g., biological samples), IM-MS can easily distinguish between molecules of different molecular class. For example, FIG. 12 illustrates the separation of peptides 356-357, oligonucleotides 358-362, and carbon clusters derived from $C_{60}$ 364 and $C_{70}$ 363 (the latter are used as both mobility and m/z internal standards). Each of these molecular classes exhibits a different trendline (353, 354, 355 for peptides, oligonucleotides, and carbon clusters, respectively) owing to the characteristic packing efficiency of particular molecular classes (e.g., carbon clusters>oligonucleotides>peptides>lipids etc.) [J. M. Koomen, B. T. Ruotolo, K. J. Gillig, J. A. McLean, D. H. Russell, M. Kang, K. R. Dunbar, M. Fuhrer, M. Gonin, and J. A. Schultz, *Oligonucleotide Analysis with MALDI-Ion*

*Mobility-TOFMS*, Anal. Bioanal. Chem. 373, 612-617 (2002)]. The resulting multiple trendlines 353-355 are analogous to the situation when modulating an ESI ion source coupled with IM-MS, whereby multiple trendlines are observed that arise from generating analyte ions having multiple charge states [see e.g., C. S. Hoaglund-Hyzer, A. E. Counterman, and D. E. Clemmer, *Anhydrous Protein Ions*, Chem. Rev. 99, 3037-3079 (1999), and references therein].

Figure 13A:
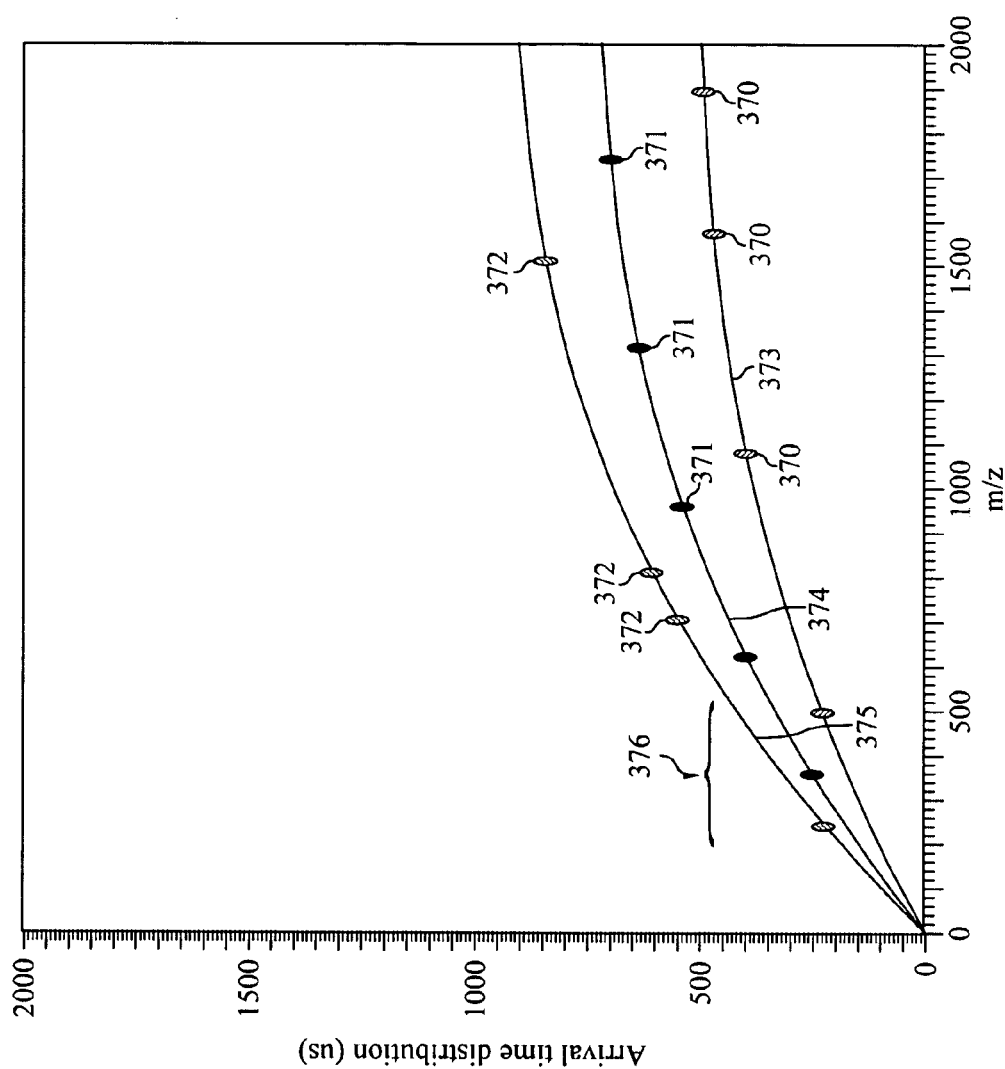
FIG. 13A. A hypothetical two-dimensional plot of the arrival time distribution vs. mass-to-charge for analytes of three different molecular classes or one molecular class consisting of three different charge-states.
Figure 13B:
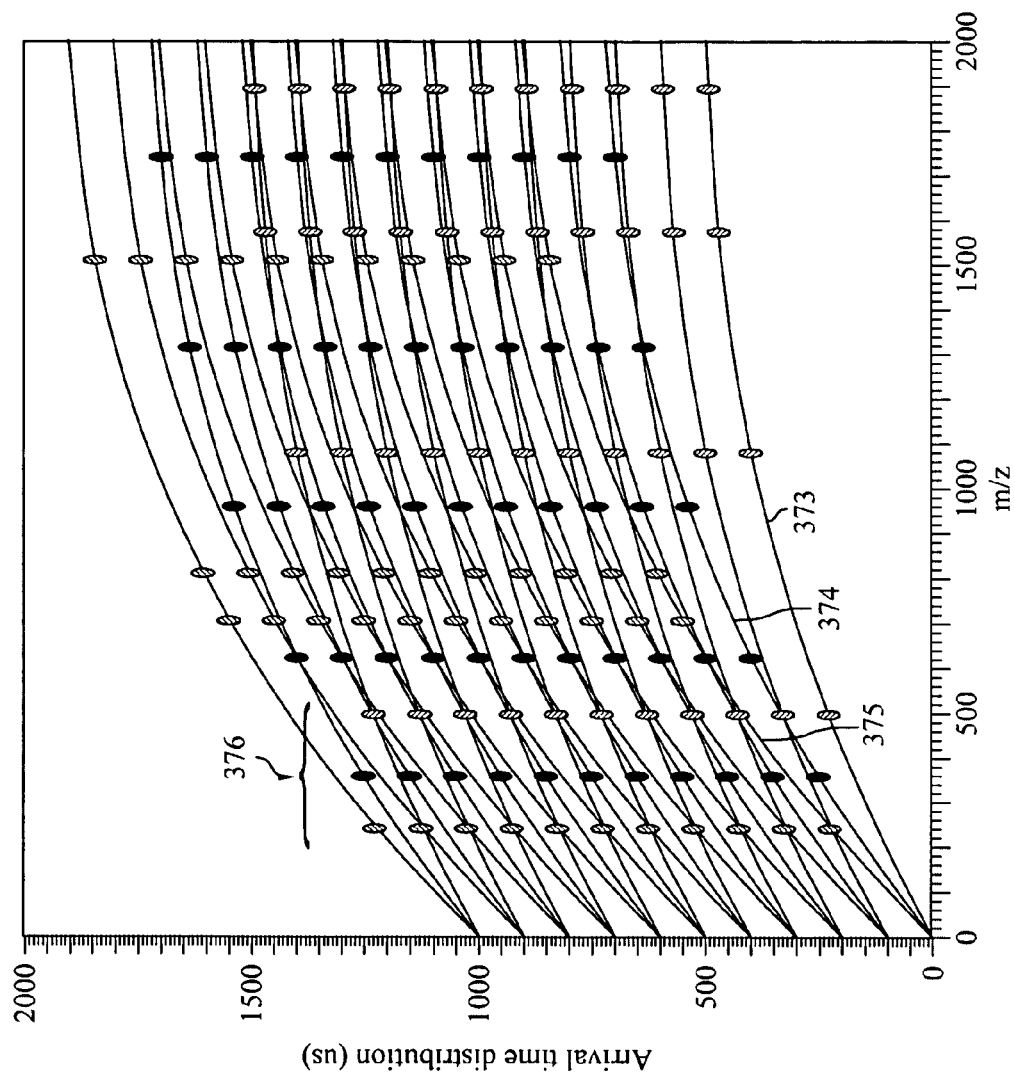
FIG. 13B. A hypothetical two-dimensional plot of the arrival time distribution vs. mass-to-charge for analytes of three different molecular classes or one molecular class consisting of three different charge-states using multiplex-mode ion injection.

Consider the hypothetical situation of multiple trendlines depicted in FIG. 13A. As noted above these trendlines 373-375 can arise from different molecular classes in MALDI (which predominantly produces singly charged ions below ca. m/z 5000), or different charge states in modulated ESI (e.g., 373=3$^+$, 374=2$^+$, and 375=1$^+$ ion signals). By using a multiplex-mode of data acquisition as described herein, there is no theoretical limitation to the number of trendlines that can be simultaneously analyzed, except for the degenerate case of two analytes on different trendlines having the exact same m/z. In the latter case the situation would be quickly apparent (as severely degraded arrival time distribution resolution after deconvolution) and can be corrected mathematically. The multiplex-mode operation in the analysis of multiple trendlines is depicted in FIG. 13B. Owing to the conserved nature of $f(t)$ for a given N, E, and molecular class, the different trendlines 373-375 are defined by the first ion injection event which serves as a frame of reference for all subsequent multiplex ion injections. Note that a priori knowledge of the number/types of analyte(s) is not necessary for accurate decoding of the modulated signals.

Figure 14:
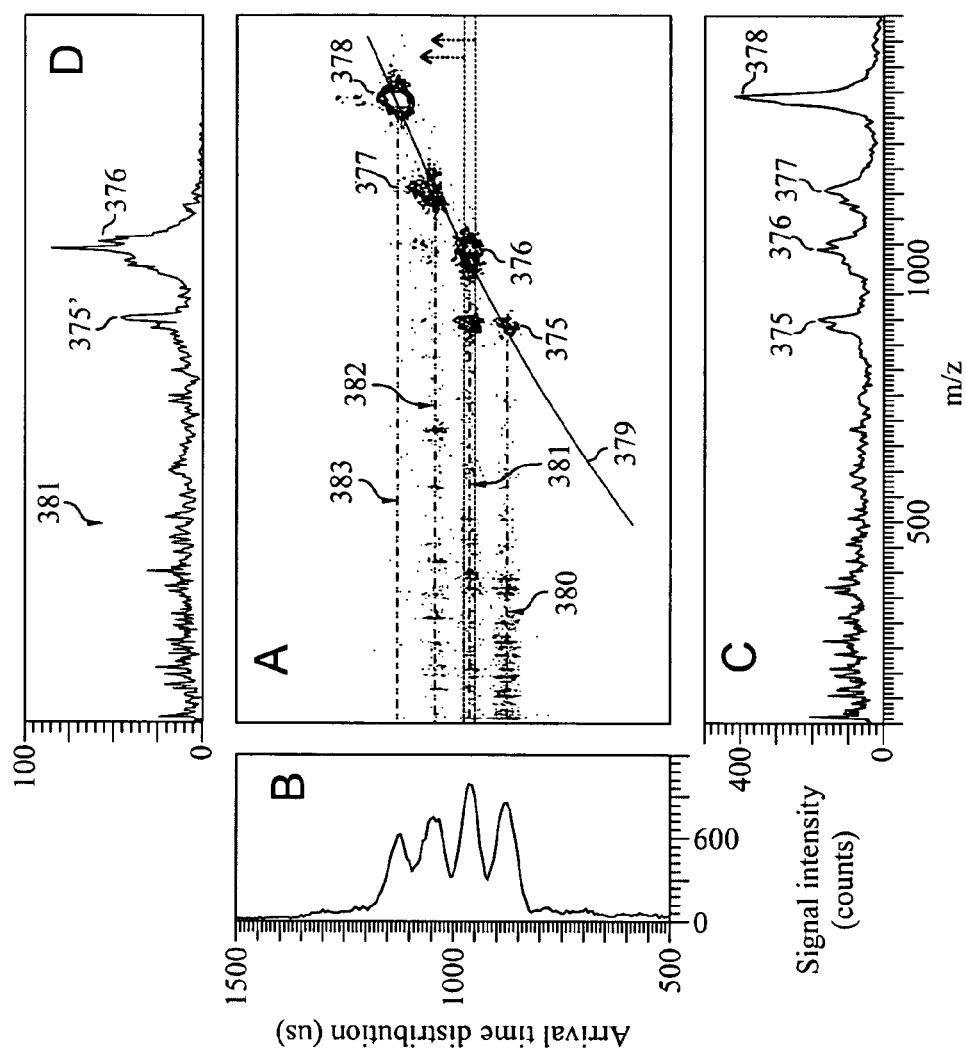
FIG. 14. (A) A two-dimensional plot of arrival time distribution vs. mass-to-charge for surface induced dissociation of four peptides after the ion mobility drift chamber and prior to mass spectrometry. (B) A plot of arrival time distribution integrated over all mass-to-charge space. (C) A plot of mass-to-charge integrated over all arrival time distribution space. (D) A plot of mass-to-charge integrated over between the two lines designated by arrows in (A).

Contemporary IM-MS can also be operated in an IM-MS/MS mode, which has parallels with conventional tandem MS/MS techniques for parent and fragment ion analysis. In IM-MS/MS operation, the IM dimension provides separation of the parent ions (similar to MS$^1$). If the ions are then activated and dissociate prior to their sampling in the MS dimension (MS$^2$), then both parent ion and fragment ion spectra are obtained nearly simultaneously [D. E. Clemmer in U.S. Pat. No. 6,559,441; Schultz et al, in U.S. Pat. No. 6,683,299 and pending U.S. application Ser. Nos. 10/689, 173, 10/967,715, and 10/969,643]. Importantly, if both the parent and the fragment ions arrive in the source of the MS at the same time, they will both be correlated to the same arrival time in the IM dimension. This is illustrated in FIG. 14, which shows both the parent ion trendline 379 and the fragment ion trendlines 380-383 for [des-Arg$_9$]-bradykinin 375, bradykinin 376, gramicidin s 377, and substance p 378, respectively. The parent ion trendline 379 is what would be observed in the absence of post-IM ion activation. In the example of FIG. 14, the parent ions are impinged onto a fluorinated-self assembled monolayer surface for dissociation as they elute from the IM drift cell, but prior to entering the source of the MS. Guideline 379 in the two-dimensional plot is to assist in visualizing the arrival time distribution-mass-to-charge correlation for the parent ions and guidelines 380-383 for visualizing the fragment ions.

Figure 15A:
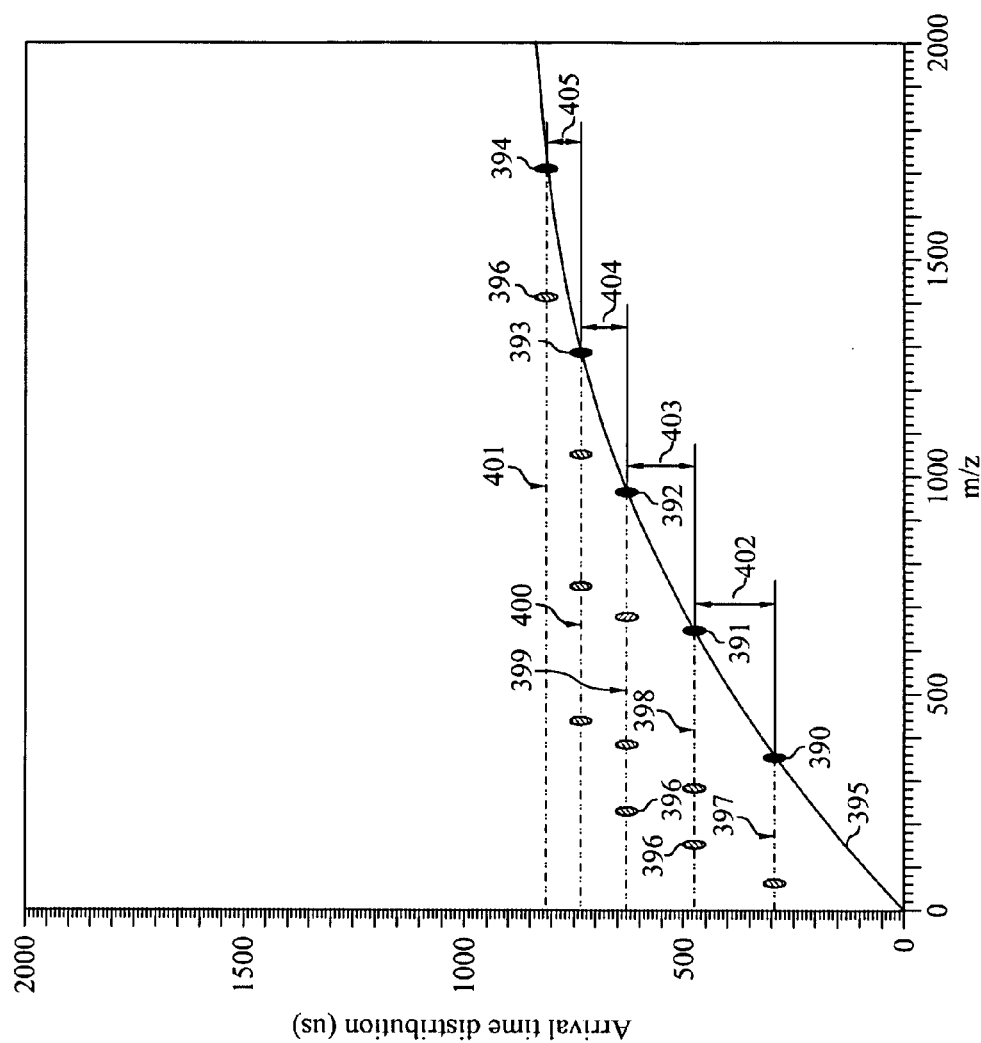
FIG. 15A. A hypothetical two-dimensional plot of the arrival time distribution vs. mass-to-charge for ion mobility followed by ion activation/dissociation prior to mass analysis.

An IM-MS/MS experiment is schematically illustrated in FIG. 15A. In this example, the parent ions 390-394 exhibit a characteristic trendline 395. As these ions elute from the IM drift cell they are activated (e.g., photo-fragmented) and dissociate prior to entering the source of the MS, so that their characteristic fragment ions 396 are arrival time correlated on fragment ion trendlines 397-401. By virtue of the parent ions being separated along the correlation function $f(t)$ 395, the fragment ion trendlines are offset from one another in arrival time Δt (402-405). In essence, almost all parent species are activated for nearly simultaneous dissociation and analysis, which in itself provides a Fellgett multiplex advantage. This is in stark contrast with contemporary MS/MS techniques whereby typically a single parent analyte is selected for fragmentation, or at best a small subset of parent ions are selected for simultaneous fragmentation (U.S. Pat. No. 4,978,852 to Williams, et al). One skilled in the art should recognize that virtually any means for activating the parent ions for dissociation can be used. These include, but are not limited to collision induced dissociation, surface induced dissociation, photodissociation, multiphoton dissociation, resonance enhanced multiphoton dissociation, blackbody induced radiative dissociation, electron capture dissociation, electron transfer dissociation, and combinations thereof. For literature example of some of these methods of activation, please see the following; collision induced dissociation [C. S. Hoaglund-Hyzer, J. Li, and D. E. Clemmer, *Mobility Labeling for Parallel CID of Ion Mixtures*, Anal. Chem. 72, 2737-2740 (2000)], surface induced dissociation [E. G. Stone, K. J. Gillig, B. T. Ruotolo, and David H. Russell, *Optimization of a Matrix-Assisted Laser Desorption Ionization-Ion Mobility-Surface Induced Dissociation-Orthogonal-Time-of-Flight Mass Spectrometer: Simultaneous Acquisition of Multiple Correlated MS1 and MS2 Spectra*, Int. J. Mass Spectrom. 212, 519-533 (2001); E. G. Stone, K. J. Gillig, B. T. Ruotolo, K. Fuhrer, M. Gonin, J. A. Schultz, and D. H. Russell, *Surface-Induced Dissociation on a MALDI-Ion Mobility-Orthogonal Time-of-Flight Mass Spectrometer: Sequencing Peptides from an "In-Solution" Protein Digest*, Anal. Chem. 73, 2233-2238 (2001)], or photodissociation [J. A. McLean, K. J. Gillig, B. T. Ruotolo, M. Ugarov, H. Bensaoula, T. Egan, J. A. Schultz, and D. H. Russell, *Ion Mobility-Photodissociation (213 nm)-Time-of-Flight Mass Spectrometry for Simultaneous Peptide Mass Mapping and Peptide Sequencing*, Proceedings of the 52nd American Society for Mass Spectrometry Conference, Montreal, Canada, June (2003) on a timescale such that dissociation occurs prior to entering the source of the MS can be used. As new ion activation techniques emerge, we envision that they too could be interfaced for application in IM-MS/MS.

Figure 15B:
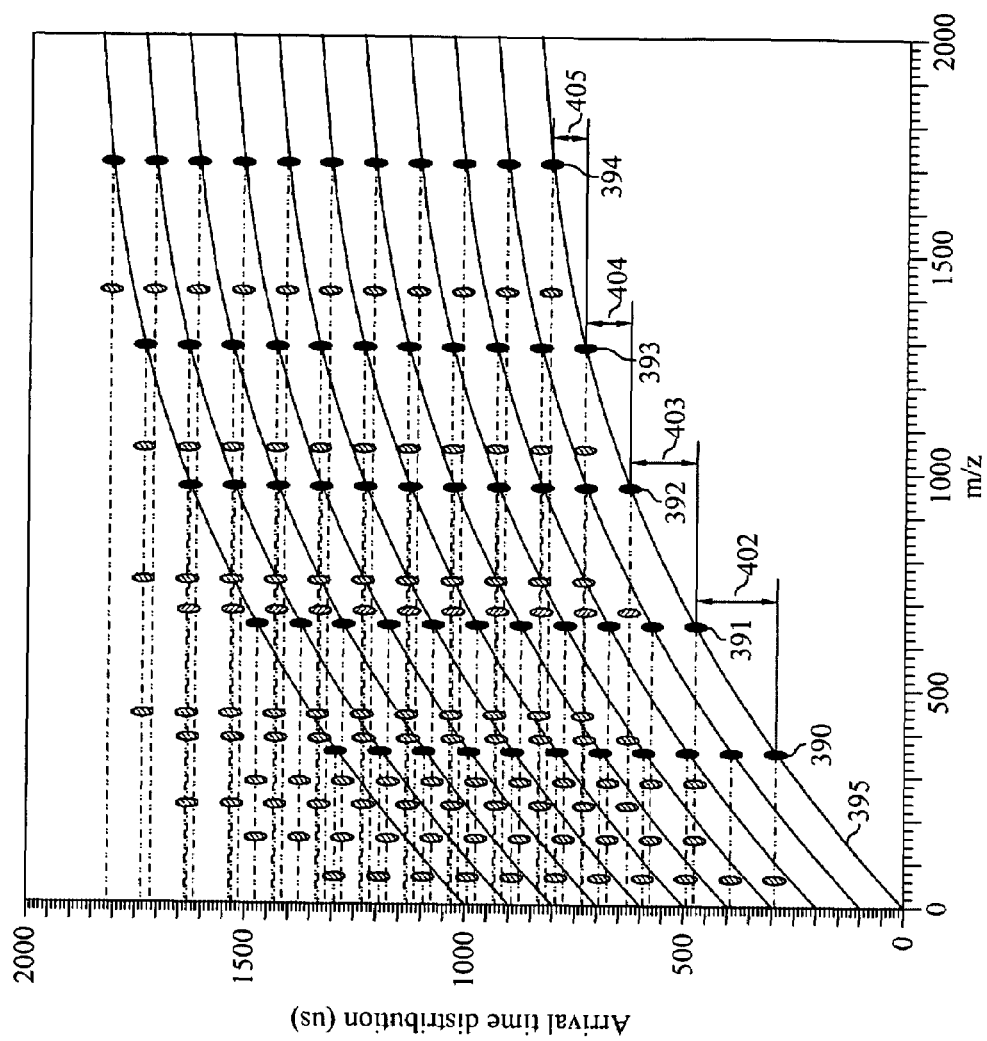
FIG. 15B. A hypothetical two-dimensional plot of the arrival time distribution vs. mass-to-charge for ion mobility followed by ion activation/dissociation prior to mass analysis using multiplex-mode ion injection of the preferred embodiment.

The correlated multiplex-mode of operation described herein is equally well suited for application in IM-MS/MS as illustrated in FIG. 15B. By determining the sequential Δt offsets 402-405 in the arrival time distribution for each correlated fragment ion trendline, both multiplex-mode parent ion spectra and multiplex-mode fragment ion spectra can be deconvoluted/decoded. From inspection of FIG. 15B, it appears that if an arrival time offset Δt (e.g., 404) is nearly the same as the time separation Δt of subsequent multiplex-mode ion injections, that fragment ions derived from multiple parent ion species (e.g., analytes 392 and 393) will exhibit nearly overlapping fragment ion trendlines and parent ion/fragment ion correlation could be lost. However, analogous to the case of multiple trendlines exhibiting different slopes for $f(t)$ (e.g., FIG. 13B) a frame of reference for the signals arising from fragment ions of a particular parent ion are readily defined by the first ion injection event. Indeed, although more challenging, it is also possible to readily demodulate/decode multiplex-mode spectra containing both multiple trendlines for molecular classes (or analyte charge-states, e.g., FIG. 13(B)) and their fragment ion correlated trendlines (e.g., FIG. 15B) in IM-MS/MS experiments.

Figure 16:
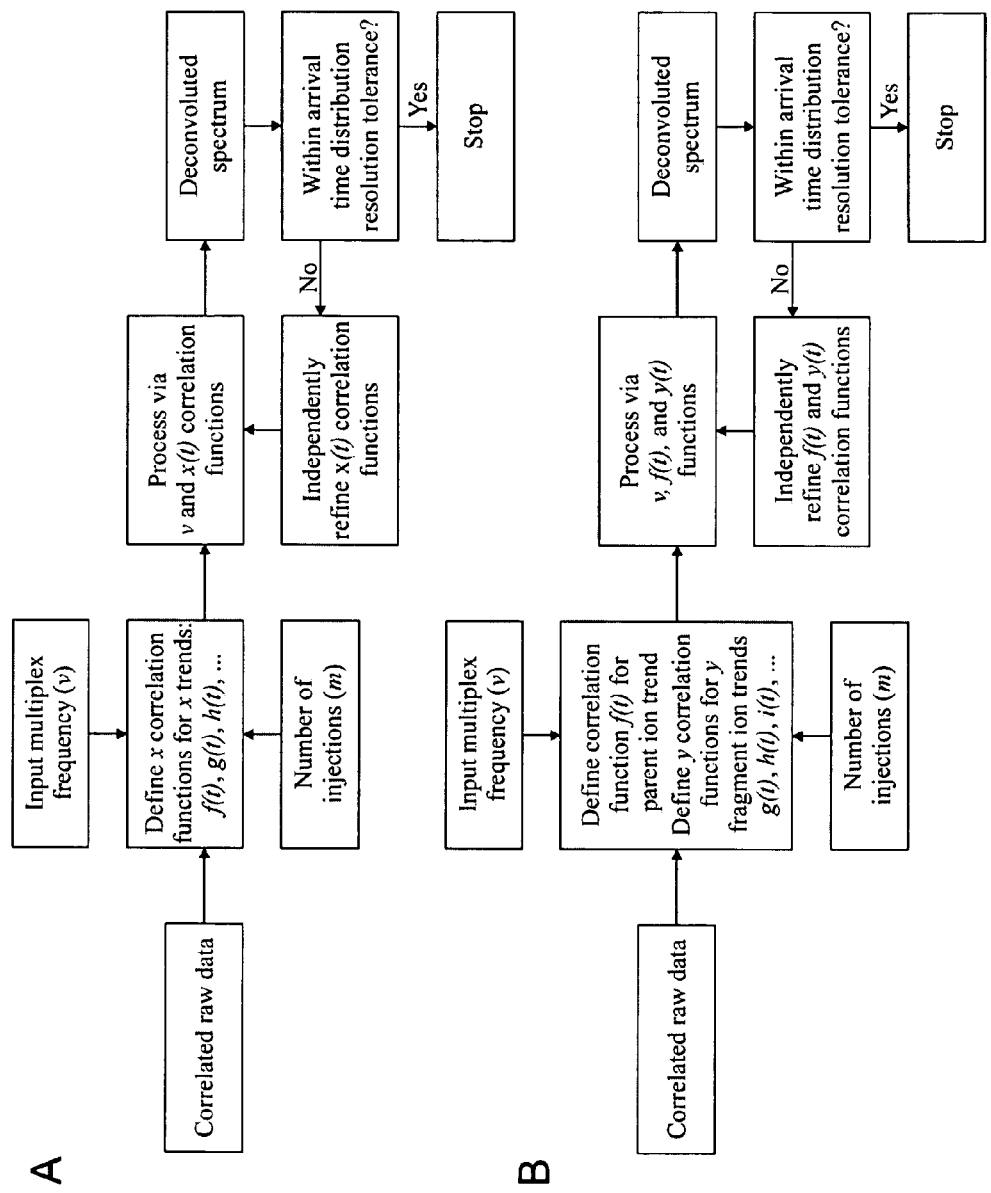
FIG. 16. (A) Post-processing scheme for deconvolution of the ion mobility arrival time distribution using multiplex-mode ion injection for the analysis of multiple molecular classes or ion charge-states (e.g., see FIG. 13(B)). (B) Post-processing scheme for deconvolution of the ion mobility arrival time distribution using multiplex-mode ion injection for ion mobility followed by ion activation/dissociation prior to mass analysis (e.g., see FIG. 15B).

A schematic flowchart for the processing of multiplex-mode spectra containing multiple trendlines is illustrated in FIG. 16A. In the case of multiple classes of ions, or charge states of analyte (e.g., FIG. 13B), the correlated raw data can be deconvoluted by defining a unique correlation function (e.g., ƒ(t), g(t), h(t) . . . etc.) for each trendline in the spectra. Along with the multiplex frequency and number of injections, each trendline correlation function can be refined again using known arrival time resolution as the convergence variable. A similar post-processing scheme for the analysis of IM-MS/MS multiplex-mode data is presented in FIG. 16B. However, in this case, a new set of correlation functions must be defined for each fragment ion/parent ion correlation. Iteration using the parent ion trendline correlation function ƒ(t), fragment ion correlation functions, and the multiplex frequency can be performed until the arrival time resolution convergence tolerance is met.

The present invention provides a means for multiplex-mode data acquisition by multiplexing ion injection into the first time dispersive dimension (i.e., IM) and demodulating the mobility phase-shifted signals by means of an ion mobility-m/z correlation determined in two-dimensions (i.e., IM-MS). In conjunction with this correlated multiplex-mode, one can realize further enhancements in signal acquisition rate by FT or HT multiplexing of the mass spectrometer dimension. In the post-processing schemes outlined in FIGS. 11 and 16, demodulation of the FT- or HT-MS signal would first be performed by application of a Fourier or Hadamard transform and followed by determination of the IM-MS correlation function. In this manner of operation, effectively two multiplex-modes of data acquisition would be performed simultaneously, i.e., one in the IM dimension and the second in the MS dimension. By using both multiplexing modes in tandem, signal enhancements (or throughput) of $10^3$ to $10^6$ can be achieved. For example, one may encode ions in the second dimension using multiplex frequency-domain analysis techniques or weighing design techniques or both and decode by application of a Fourier transform or Hadamard transform or both.

Additional dimensions of liquid- or gas-phase separations (e.g. capillary electrophoresis, capillary electrochromatography, high performance liquid chromatography, gas chromatography, etc.) can be used in a multiplexed-mode coupled with the multiplexed-mode IM-MS described herein.

The present method can be used to analyze ions of single atoms and/or molecular ions. The molecular ions may have any molecular weight, including ions of molecules possessing a molecular weight less than 500 amu, ions of molecules possessing a molecular weight less than 10,000 amu, ions of molecules possessing a molecular weight less than 100,000 amu, ions of molecules possessing a molecular weight greater than 100,000 amu, and any combination thereof.

Also within the scope of the present invention is an apparatus for ion mobility-mass spectrometry having an ion source for generating ions, an ion mobility drift cell fluidly coupled to the ion source and receiving ions from the ion source, a first timing controller coupled to the ion source, a second timing controller coupled to the ion source, a temporally-resolving mass spectrometer fluidly coupled to the ion mobility drift cell, the mass spectrometer receiving ions from the ion mobility drift cell, and a processor in communication with the ion source, the ion mobility drift cell, the first timing controller, the second timing controller, and the mass spectrometer. In preferred embodiments, the second timing controller is a burst-mode timing controller. The ion source can be any ion source, including, but not limited to the following ions sources: atmospheric pressure MALDI, ultraviolet MALDI, infrared MALDI, direct LDI, surface enhanced laser desorption/ionization, electrospray, nanospray, ion spray, photoionization, multiphoton ionization, resonance ionization, thermal ionization, surface ionization, electric field ionization, chemical ionization, atmospheric pressure chemical ionization, radioactive ionization, discharge arc/spark ionization, laser induced breakdown ionization, inductively coupled plasma ionization, direct current plasma ionization, capacitively coupled plasma ionization, glow discharge ionization, microwave plasma ionization, and any combination thereof. The ion mobility drift cell may use uniform electrostatic fields, periodic-focusing electrostatic fields, non-uniform electrostatic fields, traveling wave electrostatic fields, radiofrequency electrostatic fields, and combinations thereof. It may also use other fields. The ion mobility drift cell may utilize low-field mobility, high-field mobility, and any combination thereof. Examples of the mass spectrometer include, but are not limited to, a time-of-flight mass spectrometer, a magnetic-sector mass spectrometer, an electrostatic-sector mass spectrometer, a double-focusing sector-field mass spectrometer, a quadrupole mass spectrometer, an ion trap mass spectrometer, an ion cyclotron resonance mass spectrometer, an accelerator mass spectrometer, an orbitrap mass spectrometer, and any combination thereof.

The invention has application also to parallel processing of multiple ion signals which have been discretely input into multiple ion mobility/mass spectrometers. Recently, several patents and applications have described instruments wherein ions from one or more discrete ionization sources can be uniquely focused into each ion mobility channel within a specially constructed array of ion mobility channels (see U.S. Pat. No. 6,897,437; pending U.S. application Ser. No. 10/969,643, filed Oct. 20, 2004, both are incorporated by reference as though fully described herein), and furthermore, that the output of each ion mobility channel in such an ion array of ion mobility channels can be separately focused into its own region of a position sensitive detector within a mass spectrometer (see pending U.S. application No. 60/685,247, filed May 27, 2005; U.S. application No. 60/685,240, filed May 27, 2005; U.S. application Ser. No. 10/689,173, filed Oct. 20, 2003; U.S. application Ser. No. 10/967,715, filed Oct. 18, 2004 and U.S. Pat. No. 6,683,299, issued Jan. 27, 2004, all of which are incorporated by reference as though fully described herein). In this way, one may correlate the mass spectrometric signal corresponding to the output of each ion mobility channel. The present invention can be used in such cases to increase the ion throughput of each of the individual channels within the array of ion mobility and mass detection channels (provided by the discrete mobility tubes each feeding ions through the mass spectrometer to either discrete ion detectors or discrete regions of a position sensitive ion detector within the mass spectrometer). An example of this would be when multiple laser beams are focused into multiple locations on a surface from which ions are desorbed. Ions from each discrete location are focused into their own single, discrete ion mobility channel within a multiple channel ion mobility spectrometer which is itself fluidly connected to a position sensitive mass spectrometer. Each of the resulting mobility and mass spectra can then be unambiguously correlated with a specific location on the sample. By using the teachings of the present invention applied to each individual laser beam, each individual mobility channel, and each individual mass spectrometer channel within the array, the overall throughput of the total spectrometer can be increased. Other non-exhaustive examples would include parallel processing of the outputs of an array of ion traps, an array of electrospray sources, or the output of a field emitter array. Ions within a spatially delocalized area or volume, which would include an elongated ion beam or from a delocalized plasma, could be partitioned into each of the multiple ion mobility/mass channels so that each ion mobility and mass channel would be filled and processed according to the teachings of the present invention.

The present method can be used to analyze both ions and post-ionized neutrals of single atoms and/or molecular ions (i.e., ionization of gas phase neutral molecules) by sequential application of two or more ionization techniques. A non limiting example would use a series of steps for creating and analyzing both the directly desorbed ions and the subsequently post-ionized directly desorbed neutral species in the case of direct laser desorption of ions and neutrals from a surface using a microfocused laser or ion beam. The steps of the analysis would be 1) desorption of ions and neutrals by impinging, for example, a micro-focused laser or ion beam or beams onto one or more spots on the surface; 2) extraction of the directly ejected ions into one or more of the ion mobility-mass spectrometry analysis channels 3) post-ionization of the slowly evolving neutral gas plume after a fixed time delay which may be chosen from a range of several hundred nanoseconds to several microseconds 4) repetition of steps 1, 2, and 3 at a rate which will generate desirable statistics and which will over-fill the individual ion mobility-mass spectrometry channels, and 5) use of the deconvolution techniques described in the present invention so that two plots of ion mobility and mass can be reconstructed; one plot for the directly desorbed ions and one plot for the subsequently post-ionized directly desorbed neutrals. It is also clear that it may be desirable in certain applications to analyze only desorbed ions or only post-ionized neutral species after deflecting the directly desorbed ions thus preventing their penetration into the ion mobility channels.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An apparatus for ion mobility-mass spectrometry comprising:
   a ion source for generating gaseous ions and neutral species;
   an ion mobility drift cell fluidly coupled to said ion source and receiving ions from said ion source;
   a first timing controller coupled to said ion source;
   a second timing controller coupled to said ion source, said second timing controller is a burst-mode timing controller;
   a temporally-resolving mass spectrometer fluidly coupled to said ion mobility drift cell, said mass spectrometer receiving ions from said ion mobility drift cell; and,
   a processor in communication with said ion source, said ion mobility drift cell, said first timing controller, said second timing controller, and said mass spectrometer.

2. The apparatus of claim 1, wherein said ion source is selected from the group consisting of laser desorption/ionization, electrospray, desorption electrospray ionization, nanospray, ion spray, photoionization, multiphoton ionization, resonance ionization, thermal ionization, surface ionization, electric field ionization, chemical ionization, atmospheric pressure chemical ionization, radioactive ionization, discharge arc/spark ionization, laser induced breakdown ionization, inductively coupled plasma ionization, direct current plasma ionization, capacitively coupled plasma ionization, glow discharge ionization, microwave plasma ionization, and any combination thereof.

3. The apparatus of claim 2, wherein said laser desorption/ionization is selected from the group consisting of MALDI, direct LDI, surface enhanced laser desorption/ionization, and any combination thereof.

4. The apparatus of claim 1, wherein said ion mobility drift cell produces an electric field selected from the group consisting of uniform electrostatic fields, periodic-focusing electrostatic fields, non-uniform electrostatic fields, traveling wave electrostatic fields, radiofrequency electrostatic fields, and combinations thereof.

5. The apparatus of claim 1, wherein said ion mobility drift cell utilizes low-field mobility, high-field mobility, and any combination thereof.

6. The apparatus of claim 1, wherein said mass spectrometer is selected from the group consisting of a time-of-flight mass spectrometer, a magnetic-sector mass spectrometer, an electrostatic-sector mass spectrometer, a double-focusing sector-field mass spectrometer, a quadrupole mass spectrometer, an ion trap mass spectrometer, an ion cyclotron resonance mass spectrometer, an accelerator mass spectrometer, an orbitrap mass spectrometer, and any combination thereof.

* * * * *

UNITED STATES PATENT AND TRADEMARK OFFICE
CERTIFICATE OF CORRECTION

PATENT NO. : 7,388,197 B2  
APPLICATION NO. : 11/191666  
DATED : June 17, 2008  
INVENTOR(S) : John A. McLean et al.

Page 1 of 1

It is certified that error appears in the above-identified patent and that said Letters Patent is hereby corrected as shown below:

On the Title Page, Item (73) Assignee should read

--(73)   Assignee:   Ionwerks, Inc., Houston, TX (US)  
The Texas A & M University System, College Station, TX (US)--

Signed and Sealed this  
Fifteenth Day of April, 2014

Michelle K. Lee  
*Deputy Director of the United States Patent and Trademark Office*